United States Patent
Kimoto et al.

(10) Patent No.: US 9,655,581 B2
(45) Date of Patent: *May 23, 2017

(54) MEDICAL IMAGE DIAGNOSTIC APPARATUS

(71) Applicant: TOSHIBA MEDICAL SYSTEMS CORPORATION, Otawara-Shi (JP)

(72) Inventors: Tatsuya Kimoto, Otawara (JP); Kazumasa Arakita, Nasushiobara (JP); Yoshihiro Ikeda, Sakura (JP); Shinsuke Tsukagoshi, Nasushiobara (JP); Yasuko Fujisawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/766,184

(22) Filed: Feb. 13, 2013

(65) Prior Publication Data

US 2013/0208851 A1 Aug. 15, 2013

(30) Foreign Application Priority Data

Feb. 14, 2012 (JP) .................................. 2012-029298
Feb. 14, 2012 (JP) .................................. 2012-029313
Feb. 24, 2012 (JP) .................................. 2012-038313

(51) Int. Cl.
*A61B 6/03* (2006.01)
*A61B 6/00* (2006.01)

(52) U.S. Cl.
CPC ................ *A61B 6/54* (2013.01); *A61B 6/461* (2013.01); *A61B 6/463* (2013.01); *A61B 6/5229* (2013.01);
(Continued)

(58) Field of Classification Search
CPC ....... A61B 6/461; A61B 6/463; A61B 6/5229; A61B 6/5247; A61B 6/5288; A61B 6/542
(Continued)

(56) References Cited

U.S. PATENT DOCUMENTS 5,991,356 A * 11/1999 Horiuchi et al. ................. 378/8
6,032,536 A * 3/2000 Peeters ...................... G01L 1/20
73/725

(Continued)

FOREIGN PATENT DOCUMENTS

JP 2004-147930 A 5/2004
JP 2004-304425 A 10/2004
(Continued)

OTHER PUBLICATIONS

U.S. Appl. No. 13/766,983, filed Feb. 14, 2013, Kimoto, et al.
(Continued)

*Primary Examiner* — Glen Kao
(74) *Attorney, Agent, or Firm* — Oblon, McClelland, Maier & Neustadt, L.L.P.

(57) ABSTRACT

Provided is a medical image diagnostic apparatus, including: a collection unit for collecting data by performing irradiation of X-rays to a body part of a subject who is moving a joint; a processing unit for processing the collected data to form a plurality of internal images indicating the body part of the subject; an input unit for inputting occurrence information indicating a biological reaction that accompanies movement of the joint; a display control unit for displaying information on a display unit; and a control unit for controlling at least one of the collection unit, the processing unit, and the display control unit based on the input occurrence information.

32 Claims, 19 Drawing Sheets

(52) U.S. Cl.
CPC .......... *A61B 6/5247* (2013.01); *A61B 6/5288* (2013.01); *A61B 6/542* (2013.01)

(58) Field of Classification Search
USPC ........................................................ 378/8, 95
See application file for complete search history.

(56) References Cited

U.S. PATENT DOCUMENTS

| | | | |
|---|---|---|---|
| 6,447,163 B1* | 9/2002 | Bani-Hashemi et al. | 378/205 |
| 7,810,996 B1* | 10/2010 | Giphart | A61B 6/4441 378/205 |
| 2004/0086074 A1* | 5/2004 | Taguchi | 378/4 |
| 2006/0050840 A1* | 3/2006 | Ikeda et al. | 378/8 |
| 2007/0030957 A1* | 2/2007 | Pommi | 378/197 |
| 2007/0223649 A1* | 9/2007 | De Godzinsky | 378/4 |
| 2009/0080598 A1* | 3/2009 | Tashman et al. | 378/11 |
| 2010/0284628 A1 | 11/2010 | Uebayashi et al. | |
| 2011/0311021 A1* | 12/2011 | Tsukagoshi | 378/19 |

FOREIGN PATENT DOCUMENTS

| | | |
|---|---|---|
| JP | 2005-80059 A | 3/2005 |
| JP | 2005102937 A * | 4/2005 |
| JP | 2005-304905 A | 11/2005 |
| JP | 2005-342088 A | 12/2005 |
| JP | 2006-192151 | 7/2006 |
| JP | 2006-524548 A | 11/2006 |
| JP | 2006-528892 A | 12/2006 |
| JP | 2007-21217 A | 2/2007 |
| JP | 2007-89674 A | 4/2007 |
| JP | 2007-175258 A | 7/2007 |
| JP | 2010-154992 A | 7/2010 |
| JP | 2010-233965 A | 10/2010 |
| JP | 2010-259653 | 11/2010 |
| JP | 2011-4966 | 1/2011 |
| WO | WO 2011/126555 A2 | 10/2011 |

OTHER PUBLICATIONS

Combined Office Action and Search Report issued Aug. 28, 2014 in Chinese Patent Application No. 201310047941.6 (with English translation of category of cited documents).
Office Action issued Jan. 5, 2016 in Japanese Patent Application No. 2012-029298.
Office Action issued Jan. 5, 2016 in Japanese Patent Application No. 2012-029313.
Office Action issued Jan. 5, 2016 in Japanese Patent Application No. 2012-038313.

* cited by examiner

MEDICAL IMAGE DIAGNOSTIC APPARATUS

CROSS-REFERENCE TO RELATED APPLICATION

This application is based upon and claims the benefit of priority from Japanese Patent Applications No. 2012-029298 and No. 2012-029313, filed on Feb. 14, 2012 and No. 2012-038313, filed on Feb. 24, 2012; the entire contents of which are incorporated herein by reference.

FIELD

Embodiments relate to a medical image diagnostic apparatus.

BACKGROUND

A medical image diagnostic apparatus is an apparatus for acquiring an image expressing an internal portion of a subject. An X-ray computed tomography (CT) apparatus and an X-ray machine are known as the medical image diagnostic apparatus.

The X-ray CT apparatus is an apparatus for imaging the internal portion of the subject by scanning the subject with X-rays, collecting data, and processing the collected data by using a computer. Specifically, the X-ray CT apparatus exposes the subject to X-rays from different directions a plurality of times, detects the X-rays that have passed through the subject by using an X-ray detector, and collects a plurality of detection data pieces. The collected detection data pieces are A/D-converted by a data collecting unit and then transmitted to a data processing system. The data processing system forms projection data by subjecting the detection data to pre-processing or the like. Subsequently, the data processing system executes reconstruction processing based on the projection data to form tomographic image data.

As further reconstruction processing, the data processing system forms volume data based on a plurality of tomographic image data pieces. The volume data is a data set indicating a three-dimensional distribution of a CT value corresponding to a three-dimensional area of the subject. In a case of acquiring the volume data, a volume scan using a multi-row type X-ray detector is employed. Further, by repeatedly performing the volume scan, it is possible to acquire a plurality of volume data pieces different in time phase (4D scan).

The X-ray CT apparatus can perform multi planar reconstruction (MPR) display by rendering the volume data in an arbitrary direction. An MPR-displayed cross-sectional image (MPR image) is classified into an orthogonal three-axis image and an oblique image. The orthogonal three-axis image represents an axial image indicating an orthogonal cross-section to a body axis, a sagittal image indicating a cross-section obtained by vertically cutting the subject along the body axis, and a coronal image indicating a cross-section obtained by horizontally cutting the subject along the body axis. The oblique image is an image indicating a cross-section other than the orthogonal three-axis image. Further, the X-ray CT apparatus sets an arbitrary line of sight and renders the volume data, to thereby form a pseudo three-dimensional image obtained when the three-dimensional area of the subject is viewed from the arbitrary line of sight.

Further, the X-ray machine is an apparatus for imaging the internal portion of the subject by irradiating the subject with X-rays and detecting the X-rays that have passed therethrough by using a two-dimensional X-ray detector. A photography method using the X-ray machine is classified into normal photographing for obtaining a still image by single X-ray irradiation and fluoroscopy for obtaining the moving image by applying X-rays continuously or intermittently.

DETAILED DESCRIPTION

Embodiments provide a medical image diagnostic apparatus capable of obtaining a relationship between an action state of a body and an occurrence timing of a biological reaction. The embodiments also provide a medical image diagnostic apparatus that enables control based on a state of the biological reaction of an examinee.

The medical image diagnostic apparatus according to the embodiments includes: a collection unit configured to collect data by performing irradiation of X-rays to a body part of a subject with moving a joint of the body part; a processing unit configured to process the collected data to form a plurality of internal images indicating the body part; an input unit configured to input occurrence information indicating a biological reaction that accompanies movement of the joint; a display control unit configured to display information on a display unit; and a control unit configured to control at least one of the collection unit, the processing unit, and the display control unit based on the input occurrence information.

The medical image diagnostic apparatus according to the embodiments is described with reference to the accompanying drawings. The following description is directed to an example of an X-ray CT apparatus and an X-ray machine.

First Embodiment

Configuration

A configuration example of an X-ray CT apparatus 1 according to a first embodiment is described with reference to FIGS. 1 and 2. Note that, the terms "image" and "image data" may be regarded as having the same meaning.

Figure 1:
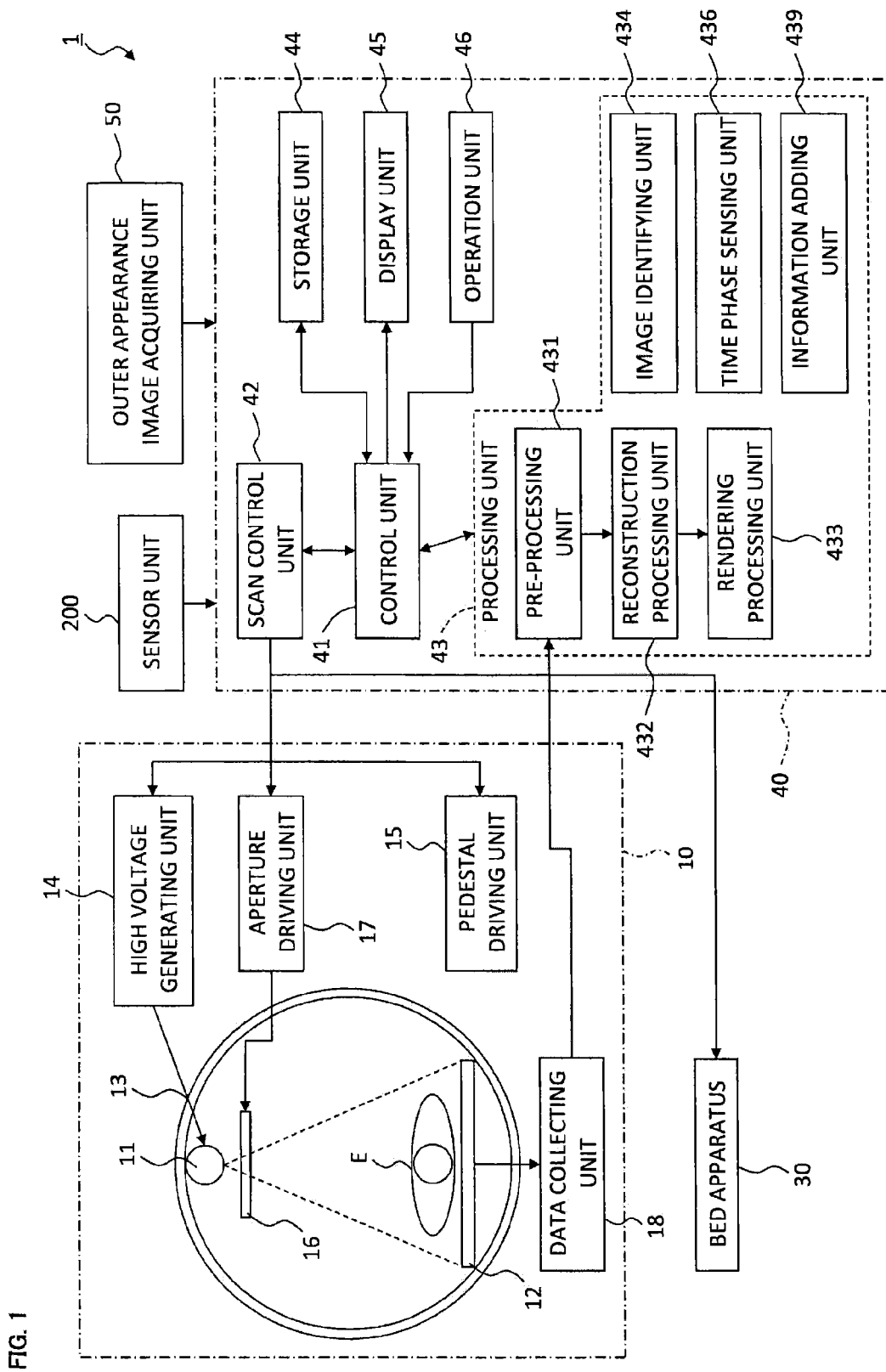
FIG. 1 is a block diagram illustrating a configuration of a medical image diagnostic apparatus (X-ray CT apparatus) according to a first embodiment.

FIG. 1 illustrates an overall configuration of the X-ray CT apparatus 1. In FIG. 2, components relating to acquisition of a CT image are collectively illustrated as an internal image acquiring unit 100. The internal image acquiring unit 100 includes a pedestal apparatus 10, a bed apparatus 30, a scan control unit 42, a pre-processing unit 431, and a reconstruction processing unit 432 that are illustrated in FIG. 1. Further, in a case where the reconstruction processing unit 432 forms volume data, the internal image acquiring unit 100 also includes a rendering processing unit 433.

This embodiment is described by taking the X-ray CT apparatus as an example, but can be applied to an MRI apparatus instead of the X-ray CT apparatus. The MRI apparatus uses a nuclear magnetic resonance (NMR) phenomenon to magnetically excite nuclear spins within a desired body part to be examined of the subject placed in a static magnetic field with a radio-frequency signal having a Larmor frequency, measures a density distribution, a relaxation time distribution, or the like based on a free induction decay (FID) signal and an echo signal that occur along with the excitement, and displays an image of an arbitrary cross-section of the subject based on data on measurement thereof.

As illustrated in FIG. 1, the X-ray CT apparatus 1 includes the pedestal apparatus 10, the bed apparatus 30, a console device 40, and an outer appearance image acquiring unit 50.

(Pedestal Apparatus)

The pedestal apparatus 10 is an apparatus for exposing a subject E to X-rays and collecting detection data on the X-rays that have passed through the subject E. The pedestal apparatus 10 includes an X-ray generating unit 11, an X-ray detecting unit 12, a rotary member 13, a high voltage generating unit 14, a pedestal driving unit 15, an X-ray aperture unit 16, an aperture driving unit 17, and a data collecting unit 18.

The X-ray generating unit 11 includes an X-ray tube (for example, a vacuum tube (not shown) for generating a cone-shaped beam or a pyramid-shaped beam) for generating X-rays. The subject E is exposed to the generated X-ray.

The X-ray detecting unit 12 includes a plurality of X-ray detecting elements (not shown). The X-ray detecting unit 12 uses the X-ray detecting element to detect X-ray intensity distribution data (hereinafter referred to also as "detection data") indicating an intensity distribution of the X-rays that have passed through the subject E, and outputs the detection data as a current signal.

As the X-ray detecting unit 12, for example, a two-dimensional X-ray detector (planar detector) in which a plurality of detection elements are arranged along each of two directions (slice direction and channel direction) orthogonal to each other is used. As the plurality of X-ray detecting elements, for example, 320 rows are provided along the slice direction. By thus using a multi-row X-ray detector, a three-dimensional area having a width in the slice direction can be photographed with a scan of one rotation (volume scan). Note that, the slice direction corresponds to a body axis direction of the subject E, and the channel direction corresponds to a rotational direction of the X-ray generating unit 11.

The rotary member 13 is a member for supporting the X-ray generating unit 11 and the X-ray detecting unit 12 in positions opposed to each other across the subject E. The rotary member 13 includes an opening portion that penetrates in the slice direction. A top board on which the subject E is placed is inserted into the opening portion. The rotary member 13 is caused to rotate along a circular trajectory about the subject E by the pedestal driving unit 15.

The high voltage generating unit 14 applies a high voltage to the X-ray generating unit 11. The high voltage is defined by parameters such as the tube voltage, the tube current, and an irradiation time (photographing time). The X-ray generating unit 11 generates X-rays based on the high voltage. The X-ray aperture unit 16 forms a slit (opening), and changes a size and a shape of the slit, to thereby adjust a fan angle (angle of divergence in the channel direction) of the X-rays output from the X-ray generating unit 11 and a cone angle (angle of divergence in the slice direction) of the X-rays. The aperture driving unit 17 drives the X-ray aperture unit 16 to change the size and the shape of the slit.

The data collecting unit 18 (data acquisition system; DAS) collects the detection data from the X-ray detecting unit 12 (each of the X-ray detecting elements). In addition, the data collecting unit 18 converts the collected detection data (current signal) into a voltage signal, integrates and amplifies the voltage signal periodically, and converts the resultant into a digital signal. Then, the data collecting unit 18 transmits the detection data that has been converted into the digital signal to the console device 40.

(Bed Apparatus)

The subject E is placed on the top board (not shown) of the bed apparatus 30. The bed apparatus 30 causes the subject E placed on the top board to move in the body axis direction. Further, the bed apparatus 30 causes the top board to move in a vertical direction.

(Console Device)

The console device 40 is used to input an operation to the X-ray CT apparatus 1. Further, the console device 40 reconstructs CT image data (tomographic image data and volume data) indicating an internal form of the subject E from the detection data input from the pedestal apparatus 10. The console device 40 includes a control unit 41, the scan control unit 42, a processing unit 43, a storage unit 44, a display unit 45, and an operation unit 46.

The control unit 41, the scan control unit 42, and the processing unit 43 include, for example, a processing device and a storage device. As the processing device, for example, a central processing unit (CPU), a graphic processing unit (GPU), or an application specific integrated circuit (ASIC) is used. The storage device includes, for example, a read only memory (ROM), a random access memory (RAM), and a hard disc drive (HDD).

Computer programs for executing functions of respective components of the X-ray CT apparatus 1 are stored on the storage device. The processing device realizes the above-mentioned functions by executing those computer programs. The control unit 41 controls the respective components of the X-ray CT apparatus 1.

The control unit 41 includes a main control unit 411, a collection control unit 412, a display control unit 413, and a processing control unit 414.

The main control unit 411 performs overall control of the X-ray CT apparatus 1. For example, the main control unit 411 controls the collection control unit 412, the display control unit 413, and the processing control unit 414. The main control unit 411 can independently control each of the components 412 to 414, and can perform cooperative control of at least two of those components 412 to 414.

The collection control unit 412 is controlled by the main control unit 411 to generate a control signal for scan and send the control signal to the scan control unit 42. Based on the control signal, the scan control unit 42 performs control described later on the high voltage generating unit 14, the pedestal driving unit 15, the aperture driving unit 17, and the bed apparatus 30, to thereby scan the subject E by using the X-rays. The control signal includes a setting value of a predetermined scan condition.

The collection control unit 412 collects the data on the body part of the subject who is moving the joint. The body part of the subject on which the data is to be collected is a movable body part such as a joint. The movable body part is described by taking an example of a part formed of two bones and a joint connecting the bones to each other. The joint located at a point joining the bones includes a synovial fluid, a synovial membrane, and a joint capsule, and has cartilages connected to the bones, which enables the movable body part to move smoothly. In other words, the bones also include the cartilages. Further, the movable body part is formed of a plurality of constituent body parts, and in the example of the above-mentioned case, the constituent body parts include the two bones connected by the joint. The examples of the movable body part include not only bones but also muscles. Note that, an object to be photographed is not limited to the joint. As a result of moving the joint, a body part other than the joint may exhibit a change, and the body part that has exhibited the change may be set as the object to be photographed. Further, it is possible that the cartilages move in accordance with the movement of the joint, and the object to be photographed may be set in accordance with the movement of the cartilages, which includes a broad meaning that the object to be photographed may be set in accordance with the movement derived from the movement of the joint.

Examples of the scan condition include a tube voltage, a tube current, a photographing time, and an irradiation interval. The tube voltage is an acceleration voltage of an electron within the X-ray generating unit 11 (X-ray tube). The tube current is an electric current caused by an electron current within the X-ray generating unit 11. The photographing time is a time for exposing the X-rays. The irradiation interval is a time interval for applying the X-rays. Note that, (the irradiation interval)=0 means continuous irradiation, and (irradiation interval)≠0 means intermittent irradiation. Such scan conditions are examples of a condition (X-ray irradiation condition) set in relation to the irradiation of the X-rays.

The display control unit 413 is controlled by the main control unit 411 to generate the control signal for display and send the control signal to the display unit 45. Further, the display control unit 413 is controlled by the main control unit 411 to process the information to be subjected to the display and send the processed information to the display unit 45. The display unit 45 displays information such as various screens, images, and texts based on at least one of the control signal and the processed information.

The processing control unit 414 is controlled by the main control unit 411 to generate the control signal for processing and send the control signal to the processing unit 43. In this embodiment, the control signal is transmitted to at least one of the reconstruction processing unit 432 and an information adding unit 439. In response to the control signal, the reconstruction processing unit 432 sets, for example, a reconstruction condition. Further, in response to the control signal, the information adding unit 439 adds predetermined additional information to image data. Those kinds of processing are described later.

Note that, the main control unit 411 can also be configured to send the control signal to the other components of the processing unit 43, for example, the pre-processing unit 431 and the rendering processing unit 433. In that case, the pre-processing unit 431 sets a condition for so-called pre-processing for generating projection data from a detection signal received from the data collecting unit 18 based on the control signal. Further, the rendering processing unit 433 sets a condition for rendering processing for generating another piece of image data from volume data based on the control signal. Further, in a case where another component is provided to the processing unit 43, in the same manner, based on the control signal received from the processing control unit 414, the another component executes predetermined processing and sets a condition for the predetermined processing.

The scan control unit 42 integrally controls operations relating to the scan using X-rays. The integral control includes control of the high voltage generating unit 14, control of the pedestal driving unit 15, control of the aperture driving unit 17, and control of the bed apparatus 30.

In the control of the high voltage generating unit 14, the high voltage generating unit 14 is controlled so as to apply a predetermined high voltage to the X-ray generating unit 11 at a predetermined timing. In the control of the pedestal driving unit 15, the pedestal driving unit 15 is controlled so as to rotationally drive the rotary member 13 with a predetermined speed at a predetermined timing. In the control of the aperture driving unit 17, the aperture driving unit 17 is controlled so that the X-ray aperture unit 16 forms the slit having a predetermined size and a predetermined shape. In the control of the bed apparatus 30, the bed apparatus 30 is controlled so as to move the top board in a predetermined position at a predetermined timing.

Note that, in the volume scan, a scan is executed with the top board fixed in position. Further, in a helical scan, a scan is executed with the top board being moved.

The processing unit 43 executes various kinds of processing on the data input from the pedestal apparatus 10 (the data collecting unit 18) and the data input from the outer appearance image acquiring unit 50. The processing unit 42 includes the pre-processing unit 431, the reconstruction processing unit 432, the rendering processing unit 433, an image identifying unit 434, and a time phase sensing unit 436.

The pre-processing unit 431 generates projection data by executing pre-processing on the detection data input from the pedestal apparatus 10. The pre-processing includes logarithmic conversion processing, offset cancellation, sensitivity correction, and beam hardening correction.

The reconstruction processing unit 432 generates the CT image data (tomographic image data and volume data) based on the projection data generated by the pre-processing unit 431. As reconstruction processing for the tomographic image data, an arbitrary method including, for example, a two-dimensional Fourier transform method or a convolution back-projection method can be employed.

The volume data is generated by performing interpolation processing on a plurality of tomographic image data pieces that have been reconstructed. As the reconstruction processing for the volume data, an arbitrary method including, for example, a cone beam reconstruction method, a multi-slice reconstruction method, or an enlargement reconstruction method can be employed. In the volume scan using the above-mentioned multi-row X-ray detector, it is possible to reconstruct the volume data within a wide range.

The reconstruction processing is executed based on the reconstruction condition set in advance. The reconstruction condition includes various items (hereinafter also referred to as "condition items"). Examples of the condition items include a field of view (the FOV), a reconstruction function, and a cross-section interval. The FOV is a condition item for defining a size of the field of view. The reconstruction function is a condition item for defining image quality characteristics and the like such as a contrast and a resolution. The cross-section interval is a condition item for defining an interval between cross-sections represented by tomographic images to be restructured, in other words, a distance between the cross-sections that are adjacent to and parallel with each other.

The reconstruction condition may be set automatically or manually. As an example of automatic setting, there is a method of selectively employing contents set in advance for each body part to be photographed in accordance with designation of the body part to be photographed or the like. Further, in this embodiment, the cross-section interval is automatically set based on a detection result for the biological reaction of the subject E, details of which are described later. Note that, not only the cross-section interval but also the FOV and the reconstruction function may be automatically set based on the detection result for the biological reaction. Further, as an example of manual setting, there is a method of displaying a predetermined reconstruction condition setting screen on the display unit 45 and operating the reconstruction condition setting screen by using the operation unit 46.

The rendering processing unit 433 can execute, for example, MPR processing and volume rendering. The MPR processing is image processing for setting an arbitrary cross-section for the volume data generated by the reconstruction processing unit 432 and subjecting the cross-section to rendering processing, to thereby generate an MPR image data indicating the cross-section. The volume rendering is image processing for sampling the volume data along an arbitrary line of sight (ray) and accumulating values (CT values) thereof, to thereby generate pseudo three-dimensional image data indicating the three-dimensional area of the subject E.

(Image Identifying Unit)

First, a description is made of matters on which the processing executed by the image identifying unit 434 is predicated. The image (CT image) formed by the reconstruction processing unit 432 is referred to as "internal image", and the image acquired by the outer appearance image acquiring unit 50 is referred to as "outer appearance image". The internal image is an image that represents an interior of the subject E. Further, the outer appearance image is an image that represents an outer appearance of the subject E.

The internal image acquiring unit 100 continuously or intermittently irradiates a predetermined body part of the subject E with X-rays to acquire the plurality of internal images. The predetermined body part is, for example, a joint part. Examples of the plurality of internal images include a plurality of volume data pieces along time series obtained by a 4D scan, a pseudo three-dimensional image or a plurality of tomographic images along time series obtained by rendering those volume data pieces, and a plurality of tomographic images along time series obtained by repeatedly scanning a predetermined cross-section.

The operation unit 46 is used to input occurrence information indicating an occurrence of the biological reaction of the subject E. The biological reaction includes one that occurs along with a pain. Examples of the biological reaction that occurs along with a pain include recognition of the pain, utterance, a change in facial expression, a change in respiration, a change in perspiration, a change in electrocardiogram, a change in blood pressure, a change in electromyogram, a change in electroencephalogram, and a change in pupil diameter. The biological reaction that accompanies the movement of the joint is exemplified as described above, and the movement of the joint itself can be assumed as the biological reaction, but the present invention is not limited thereto. The operation unit 46 may be operated along with the movement of the joint, or a detection operation may be effected by a sensor unit 200 described later.

An operator of the operation unit 46 operates the operation unit 46 in response to the occurrence of such a biological reaction. The operation unit 46 that has received the operation inputs a signal serving as the occurrence information to the control unit 41. Note that, the operator is the subject E (patient) or another person (such as doctor, nurse, or radiological technologist).

The outer appearance image acquiring unit 50 acquires the outer appearance image by photographing the predetermined body part of the subject E at least at a photographing timing corresponding to the input of the occurrence information. The photographing may be any one of still image photographing and moving image photographing. The outer appearance image acquiring unit 50 is described later in detail.

With the above-mentioned preparations made, the image identifying unit 434 is described. The image identifying unit 434 includes a function of identifying the internal image acquired at substantially the same time as the input of the occurrence information (first identification unit) and a function of identifying the outer appearance image acquired at substantially the same time as the input of the occurrence information (second identification unit). Those functions are now described.

The image identifying unit 434 identifies the internal image acquired at substantially the same time as the input of the occurrence information among the plurality of internal images acquired by the internal image acquiring unit 100. Note that, as described later, the processing for identifying the internal image may include the processing for identifying the outer appearance image. The control unit 41 stores the identified internal image, the outer appearance image acquired at the photographing timing corresponding to the input of the occurrence information on the biological reaction, and timing information indicating the occurrence timing of the biological reaction, in the storage unit 44 in association with one another.

Examples of the timing information include image information or character string information indicating the occurrence timing of the biological reaction and a flag indicating the occurrence timing. Examples of the character string information include a file name of each image data on the internal image and the outer appearance image and a folder name of a folder that stores each image data. Further, examples of the image information include image data stored along with each image data on the internal image and the outer appearance image and information superimposed on each image data.

Further, as in the case where the outer appearance image acquiring unit 50 performs the moving image photographing or performs the still image photographing a plurality of times, in a case where the predetermined body part of the subject E is repeatedly photographed, the image identifying unit 434 identifies the outer appearance image acquired at substantially the same time as the input of the occurrence information on the biological reaction among the sequentially-acquired outer appearance images. The processing for identifying the outer appearance image can be executed in the same manner as the processing for identifying the internal image. The control unit 41 stores the identified outer appearance image and the above-mentioned timing information in the storage unit 44 in association with each other. In addition, the control unit 41 stores at least one of the plurality of internal images acquired by the internal image acquiring unit 100 in the storage unit 44. The internal image to be stored may be the internal image identified as described above, at least one internal image selected by another method, or all the plurality of internal images.

The wording "substantially the same time" not only represents completely the same time but also allows an arbitrarily-set error. The error is determined based on, for example, an acquisition interval for at least one of the internal image and the outer appearance image. An example of the processing executed by the image identifying unit 434 is described. In the following example, a predetermined joint part of the subject E is to be examined. The internal image and the outer appearance image are obtained by photographing a range including the range including the joint part.

Figure 2:
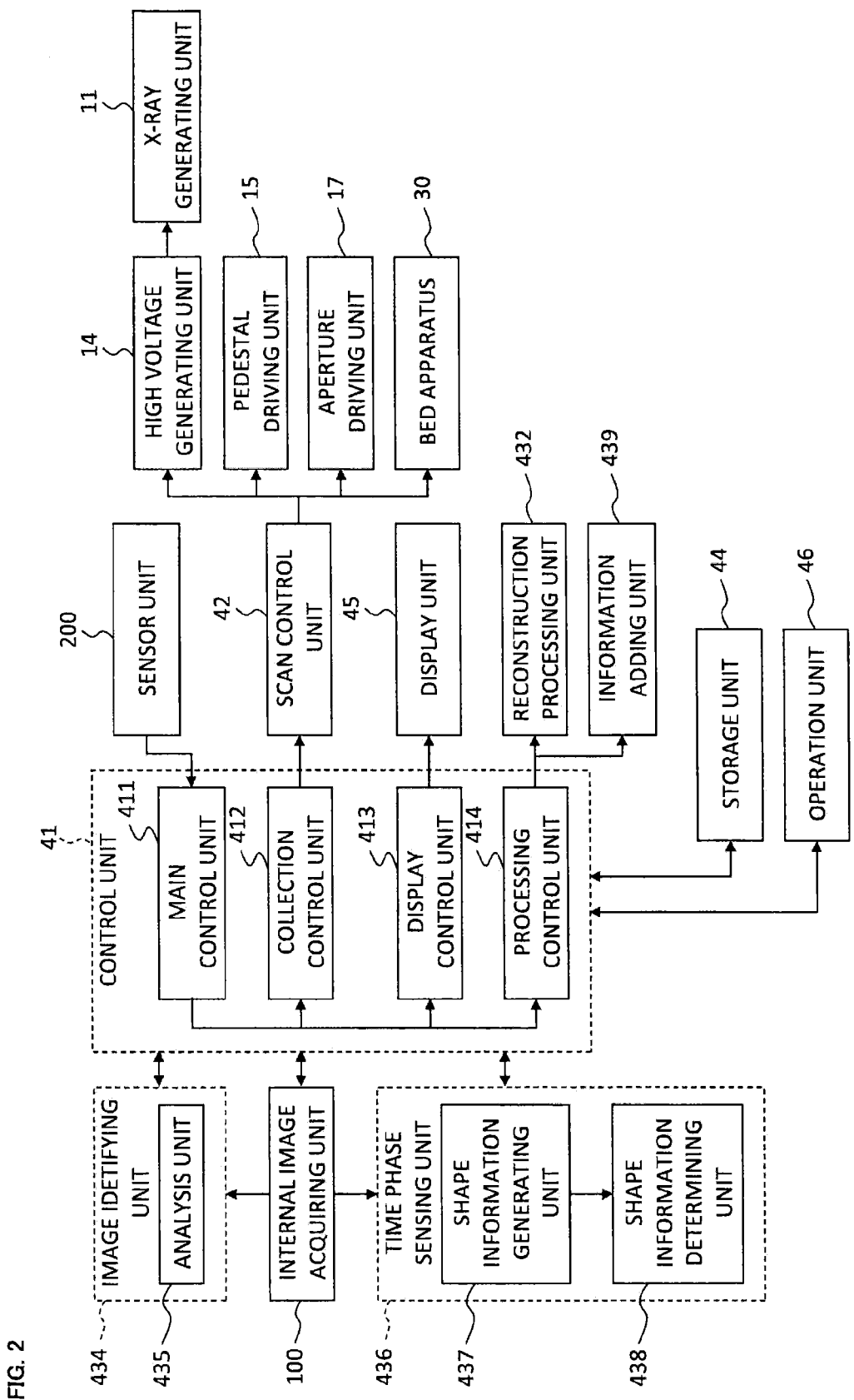
FIG. 2 is a block diagram illustrating the configuration of the medical image diagnostic apparatus (X-ray CT apparatus) according to the first embodiment.

In a case where a first processing example is employed, the image identifying unit 434 includes an analysis unit 435 as illustrated in FIG. 2. The analysis unit 435 analyzes the outer appearance image acquired by the outer appearance image acquiring unit 50, to thereby acquire first shape information indicating a shape of the joint part. In addition, the analysis unit 435 analyzes each of the plurality of internal images acquired by the internal image acquiring unit 100, to thereby acquire second shape information indicating the shape of the joint part drawn in the internal image.

Here, in the internal image and the outer appearance image, the joint part is drawn from (substantially) the same direction. As a method of realizing this, a drawing direction of the outer appearance image can be matched with a drawing direction of the internal image, and vice versa. The former is employed in the case of using the X-ray machine, and can be realized by, for example, providing a photography apparatus for the outer appearance image in the vicinity of the X-ray tube or the X-ray detector.

The latter is employed in the case of, for example, forming the volume data, and can be realized by rendering the volume data on the tomographic image of the cross-section corresponding to the drawing direction of the outer appearance image. As an example of a method of identifying the cross-section, a data range corresponding to the joint part is identified in the volume data, and a two-dimensional data range that (substantially) matches the shape of a two-dimensional area corresponding to the joint part in the outer appearance image within a three-dimensional data range thereof is identified by using the image processing such as the pattern matching, which enables an orientation of the two-dimensional data range in the coordinate system defined in the volume data to be set as an orientation of an object cross-section.

Figure 3:
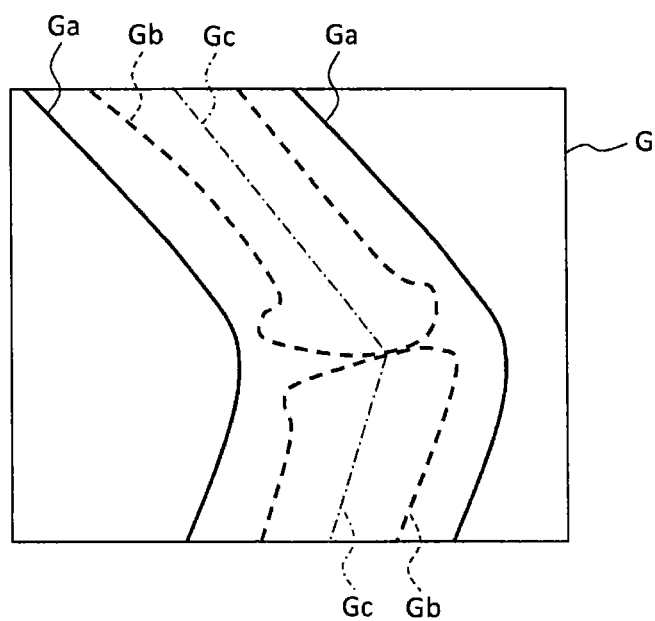
FIG. 3 is a schematic diagram illustrating processing executed by the medical image diagnostic apparatus (X-ray CT apparatus) according to the first embodiment.

Each of the first shape information and the second shape information indicates, for example, a shape of a contour of a body surface within the range including the joint part. In this case, the analysis unit 435 identifies the image area having, for example, a predetermined color (skin color) or predetermined shapes (shapes of the joint part and the surrounding body part) based on a pixel value (such as brightness value, RGB value, or CT value) of each image. In addition, the analysis unit 435 identifies the image area (contour area) corresponding to the contour of the image area. As an example of this case, FIG. 3 illustrates a contour area Ga within a CT image G. The contour area itself or the shape (including an approximate shape) corresponds to the first shape information and the second shape information.

The shape information is not limited to a contour shape, and any shape that indicates the shape of the joint part may suffice. For example, the contour shape of a bone and a core line shape thereof can be used as the shape information. As an example of those cases, FIG. 3 illustrates a contour area Gb of a bone and a core line area Gc thereof within the CT image G. Note that, in the case of using the core line shape, an angle formed by core lines of at least two bones located in the joint part may be determined, and angle information thereon may be set as the shape information. Also in the case of using the contour shape, each of directions of two body parts (for example, upper arm and forearm in the case of the elbow joint) contacting with each other in the joint part may be identified based on the contour shape and an angle formed by those two directions may be obtained, and the angle information thereon may be set as the shape information.

The analysis unit 435 performs the above-mentioned processing on each of the plurality of internal images acquired by the internal image acquiring unit 100. Accordingly, a plurality of second shape information pieces are obtained. The image identifying unit 434 identifies the internal image corresponding to a second shape information piece that substantially matches the first shape information based on the outer appearance image among the plurality of second shape information pieces that have been obtained. This processing can be performed by, for example, subjecting the first shape information and the second shape information to the image processing such as the pattern matching. The internal image identified in such a manner is used as the internal image acquired at substantially the same time as the input of the occurrence information on the biological reaction.

A second processing example is described. Also in a case where this processing example is employed, the image identifying unit 434 includes the analysis unit 435 as illustrated in FIG. 2. The analysis unit 435 analyzes the outer appearance image acquired by the outer appearance image acquiring unit 50, to thereby acquire first feature position information indicating a position of a predetermined feature area within the outer appearance image. In addition, the analysis unit 435 analyzes each of the plurality of internal images acquired by the internal image acquiring unit 100, to thereby acquire second feature position information indicating the position of the feature area within the internal image.

The feature area is an image area corresponding to a predetermined body part of a human body or an image area corresponding to an artifact photographed along with the subject E. Examples of the former include a predetermined bone or a predetermined body part thereof and a predetermined organ or a predetermined body part thereof. Further, examples of the latter include a marker attached to the subject E, an insertion (such as catheter) inserted into the subject E, and the artifact (such as bolt for connecting bones) provided to the interior of the subject E.

Processing for identifying the feature area can be, for example, performed by the pattern matching based on the shape of the feature area or performed based on the pixel value (such as brightness value, RGB value, or CT value) unique to the feature area. Further, the number of feature areas to be identified is an arbitrary number of at least one. In a case of identifying at least two feature areas, information indicating a positional relationship (such as distance and direction) between those feature areas can be set as feature position information.

Further, each feature area may be any one of one point (one pixel) and an image area formed of a plurality of pixels. In a case of the latter, the information indicating the size and the shape of the image area can be set as the feature position information.

The analysis unit 435 performs the above-mentioned processing on each of the plurality of internal images acquired by the internal image acquiring unit 100. Accordingly, a plurality of second feature position information pieces are obtained. The image identifying unit 434 identifies the internal image acquired at substantially the same time as the input of the occurrence information on the biological reaction based on the obtained plurality of second feature position information pieces and the first feature position information based on the outer appearance image.

This processing can be performed by, for example, comparing the first feature position information with the second feature position information to select the second feature position information indicating the feature area having (substantially) the same positional relationship as the positional relationship between at least two feature areas indicated by the first feature position information, (substantially) the same size or shape as those of the feature area indicated by the first feature position information, or the like. The internal image corresponding to the selected second feature position information is used as the internal image acquired at substantially the same time as the input of the occurrence information on the biological reaction.

A third processing example is described. In a case where this processing example is employed, there is no need to provide the analysis unit 435 to the image identifying unit 434 as illustrated in FIG. 1. In the case of performing this processing example, the image identifying unit 434 receives first input timing information indicating a timing at which the occurrence information on the biological reaction is input by the operation unit 46 and second input timing information indicating a timing at which the internal image is acquired by the internal image acquiring unit 100. Then, the image identifying unit 434 identifies the internal image corresponding to the second input timing information received at substantially the same time as the first input timing information.

The first input timing information is sent from the control unit 41 to the image identifying unit 434 in response to the input of the signal from the operation unit 46 to the control unit 41. The second input timing information is input to the image identifying unit 434 every time the internal image of each time phase is formed or every time the scan of each time phase is performed.

In a case where time required for the pre-processing and the reconstruction processing is sufficiently short, the second input timing information is input to the image identifying unit 434 from any one of the reconstruction processing unit 432, the rendering processing unit 433, the control unit 41, and the pedestal apparatus 10 at any one of timings for image formation and scanning. Otherwise, the second input timing information is input to the image identifying unit 434 from the control unit 41 or the pedestal apparatus 10 at a timing at which a scan is performed.

The second input timing information is successively input to the image identifying unit 434. The image identifying unit 434 that has received the input of the first input timing information corresponding to operation of the operation unit 46 identifies the second input timing information input at, for example, the closest timing to the input timing for the first input timing information. Then, the image identifying unit 434 sets the internal image corresponding to the identified second input timing information as the internal image acquired at substantially the same time as the input of the occurrence information on the biological reaction.

(Time Phase Sensing Unit)

The internal image acquiring unit 100 acquires a new internal image based on the outer appearance image and the timing information stored in the storage unit 44 under control of the control unit 41. The time phase sensing unit 436 operates in this processing. Two examples of this processing are now described.

In a first processing example, based on the outer appearance image and the timing information stored in the storage unit 44, the internal image acquiring unit 100 acquires the new internal image in a specific time phase corresponding to the timing information. The "specific time phase" is described. The timing information indicates the occurrence timing of the biological reaction. The specific time phase corresponds to a state of the predetermined body part (for example, bent state of the joint) of the subject E at the occurrence timing of the biological reaction. The specific time phase is not necessarily a time phase that completely matches the state of the predetermined body part, and allows an arbitrarily-set error. Further, the specific time phase does not need to be a single time phase and may be at least two time phases.

In this processing example, the internal image acquiring unit 100 executes photographing using X-rays having a first intensity and photographing using X-rays having a second intensity while switching therebetween. The second intensity is lower than the first intensity. The switching is executed by controlling the above-mentioned parameters of the high voltage applied to the X-ray generating unit 11 from the high voltage generating unit 14. The internal image acquiring unit 100 applies the X-rays having the first intensity in the specific time phase, and applies the X-rays having the second intensity in the time phase other than the specific time phase. Accordingly, a plurality of new internal images corresponding to a plurality of time phases including the specific time phase are acquired. In other words, the internal image acquiring unit 100 performs the photographing with X-rays having a relatively high intensity in the specific time phase, and performs the photographing with X-rays having a relatively low intensity in the time phase other than the specific time phase.

The time phase sensing unit 436 determines a timing to switch an X-ray intensity in such processing. In order to execute this processing, the time phase sensing unit 436 includes a shape information generating unit 437 and a shape information determining unit 438. The shape information generating unit 437 functions as an example of a "generation unit", and the shape information determining unit 438 functions as an example of a "determination unit".

With regard to the processing executed by the time phase sensing unit 436, a first specific example and a second specific example are described. In both the first and second specific examples, the time phase sensing unit 436 compares a newly-acquired image with the outer appearance image acquired in the past. In the first specific example, the newly-acquired internal image is used, and in the second specific example, the newly-acquired outer appearance image is used.

The first specific example is described. In the first specific example, the time phase sensing unit 436 senses arrival of the specific time phase by comparing the new internal image acquired by applying the X-rays having the second intensity (relatively low intensity) with the outer appearance image stored in the storage unit 44.

This processing is described more specifically. First, the shape information generating unit 437 analyzes each of the new internal image acquired by applying the X-rays having the second intensity and the outer appearance image stored in the storage unit 44, and generates predetermined body part shape information indicating the shape of the predetermined body part of the subject E. This processing includes, for example, the same processing as the processing executed by the image identifying unit 434. Note that, a part relating to the same processing may be executed by the image identifying unit 434. Examples of the same processing include processing for obtaining the contour, the core line, the angle, and the like of the predetermined body part within the image (the above-mentioned first processing example) and processing for obtaining the position of the feature area within the image (the above-mentioned second processing example). In those cases, the predetermined body part shape information is information indicating the shape of the contour of the predetermined body part, the shape of the core line thereof, the angle information thereon, or the positional relationship of the feature area.

The shape information determining unit 438 determines whether or not the predetermined body part shape information generated from the new internal image and the predetermined body part shape information generated from the outer appearance image stored in the storage unit 44 substantially match each other. The determination processing is the same processing as, for example, the above-mentioned pattern matching executed by the image identifying unit 434. In that case, this processing may be executed by the image identifying unit 434.

When the shape information determining unit 438 determines that the above-mentioned pieces of predetermined body part shape information substantially match each other, the time phase sensing unit 436 determines that the specific time phase has arrived. In response to the fact that the time phase sensing unit 436 has sensed the arrival of the specific time phase, the control unit 41 controls the internal image acquiring unit 100 to switch from the second intensity to the first intensity.

The second specific example is described. In the second specific example, the time phase sensing unit 436 senses the arrival of the specific time phase by comparing the new outer appearance image acquired by the outer appearance image acquiring unit 50 with the outer appearance image stored in the storage unit 44. Detailed description of this processing is omitted because the internal image used in the first specific example is merely replaced by the outer appearance image. This is the end of the description of the first processing example.

Next, a second processing example is described. In this processing example, based on the outer appearance image and the timing information stored in the storage unit 44, the internal image acquiring unit 100 acquires the new internal image during a predetermined period including the time phase corresponding to the timing information.

The first and second processing examples are different in the time phase in which the new internal image is to be acquired. In other words, in the first processing example, new photographing is performed in the specific time phase corresponding to the stored timing information, while in the second processing example, the new photographing is performed not only in the specific time phase but also during the predetermined period including the specific time phase.

The predetermined period is described. The predetermined period may have the specific time phase as a beginning stage, an end stage, or other such stage. In the case where the specific time phase is set as the beginning stage, the predetermined period can be set by, for example, measuring a period having a length determined in advance since the arrival of the specific time phase. In the case where the specific time phase is set as the end stage, for example, information indicating a predetermined time phase that arrives before the specific time phase is included in the timing information in advance. Then, a period since the arrival of the predetermined time phase until the arrival of the specific time phase can be set as the predetermined period. In the case where the specific time phase is neither the beginning stage nor the end stage, the predetermined period can be set by, for example, combining the above-mentioned two cases to determine a period before the specific time phase and a period thereafter.

In a case where there are a plurality of specific time phases, a period between those specific time phases can be set as the predetermined period. Further, the predetermined period may be formed of at least two periods. Each of those periods can be set, for example, in the above-mentioned manner.

Also in this processing example, in the same manner as the first processing example, the internal image acquiring unit 100 executes the photographing using the X-rays having the first intensity in the time phase included in the predetermined period, and executes the photographing using the X-rays having the second intensity in a time phase during a period other than the predetermined period, to thereby acquire a plurality of new internal images.

With regard to the switching of the X-ray intensity, the time phase sensing unit 436 performs the same processing as the first processing example. In other words, in the case of using the new internal image (corresponding to the above-mentioned first specific example), the time phase sensing unit 436 compares the new internal image acquired by applying the X-rays having the second intensity with the outer appearance image stored in the storage unit 44, to thereby sense the arrival of the time phase included in the predetermined period. Further, in the case of using the new outer appearance image (corresponding to the above-mentioned second specific example), the time phase sensing unit 436 compares the new outer appearance image acquired by the outer appearance image acquiring unit 50 with the outer appearance image stored in the storage unit 44, to thereby sense the arrival of the time phase included in the predetermined period.

In those processings, the shape information generating unit 437 and the shape information determining unit 438 perform the same processing as the first processing example to determine whether or not the pieces of predetermined body part shape information based on the two images substantially match each other, and when it is determined that the pieces of predetermined body part shape information substantially match each other, the time phase sensing unit 436 determines that an object time phase has arrived.

The object time phase is a time phase included in the above-mentioned predetermined period. The object time phase may be an arbitrary one of the time phases included in the predetermined period. For example, a case where a time phase other than the beginning stage and the end stage within the predetermined period is first sensed based on a speed of an action of the predetermined body part, a direction of the action, and time required for the photographing or the processing is assumed. In this processing example, even in such a case, it can be determined whether or not the time phase is included in the predetermined period.

In response to the fact that the time phase sensing unit 436 has sensed the arrival of the specific time phase, the control unit 41 controls the internal image acquiring unit 100 to switch from the second intensity to the first intensity.

The information adding unit 439 adds the predetermined additional information corresponding to the detection result for the biological reaction of the subject E to the image data. The image data is, for example, the volume data or tomographic image data that is generated by the reconstruction processing unit 432 or the image data generated by the rendering processing unit 433. Further, the image data may be image data generated by the processing unit 43 causing the reconstruction processing unit 432 or the rendering processing unit 433 to subject the image data to arbitrary image processing. Examples of the image data obtained by the arbitrary image processing include a subtraction image obtained as a difference between two pieces of image data and a fusion image obtained by combining the image data generated by the X-ray CT apparatus 1 with the image data generated by another modality. Further, the additional information means arbitrary information processed together with the image data. The term "adding" as used herein includes both addition to an outside of the image data and addition to an inside of the image data. The information adding unit 439 functions as an example of a "data processing unit". A description is made below of an example of processing executed by the information adding unit 439. Note that, a method of adding the additional information is described here, and a specific example of the processing corresponding to the detection result for the biological reaction is described later.

A first processing example is an example of the additional information to be added to the outside of the image data. The additional information of the first processing example is supplementary information in digital imaging and communications in medicine (DICOM) that is a standard relating to storage and communications of the image data. The supplementary information is generally referred to as "DICOM tag". The DICOM tag is provided with an area that enables recording of arbitrary information. The information adding unit 439 externally adds the additional information by recording predetermined supplementary information in the area for the recording within the DICOM tag.

A second processing example is an example of the additional information to be added to the inside of the image data. The additional information of the second processing example is information having a predetermined format to be embedded in the image data. The information is referred to as "embedded information". The term "embedding" as used herein means at least any one of substitution of a part of the image data with other information and generation of new image data by adding an area (in other words, pixel) for recording other information to the image data. The information adding unit 439 internally adds the additional information by executing such embedding processing on the image data.

At a time of displaying the image based on the image data, the embedded information may be invisible or visible. In a case of employing the invisible embedded information, by referring to the embedded information, it is possible to display the visible information separately from the image or with the image.

As an example of a case of employing the visible embedded information, in the image based on the image data, it is possible to embed the information in the area that does not interfere with diagnosis. The area that does not interfere with diagnosis is an area other than the area that draws the subject E, an area other than the area that draws an instrument (such as an explorer) inserted into a body, an area other than the area that draws an instrument (such as an electrode of an electrocardiograph or a marker indicating a position) attached to a surface of the body of the subject E, or other such area.

An example of the visible embedded information in a case where the image data is the volume data is described. In this example, the information adding unit 439 embeds the embedded information in a position within the volume data included in an arbitrary cross-section of the volume data. The arbitrary cross-section includes at least one of three orthogonal cross-sections of an orthogonal three-axis image obtained by the MPR processing and the cross-section of an arbitrary oblique image. The position within the volume data satisfying such a condition is, for example, at least one of a position on an entire outer peripheral surface of the volume data and a position in an inside portion in a vicinity thereof (in other words, inner portion of the outer peripheral surface by a predetermined number of pixels). Note that, if the volume data having an FOV that is truly smaller than the scanned area is generated, the embedded information for the volume data having the FOV that is truly smaller can be generated from the information embedded in the volume data having the FOV larger than the volume data having an FOV that is truly smaller (for example, volume data having an FOV of the entire scanned area).

(Storage Unit, Display Unit, and Operation Unit)

The storage unit 44 stores the detection data, the projection data, the image data obtained after the reconstruction processing, and the like. The display unit 45 is formed of a display device such as a liquid crystal display (LCD). The operation unit 46 is used to input various kinds of information and various instructions to the X-ray CT apparatus 1. The operation unit 46 is formed of, for example, a keyboard, a mouse, a trackball, a joystick, and the like. Further, the operation unit 46 may include a graphical user interface (GUI) displayed on the display unit 45.

As described above, the operation unit 46 is used to input the occurrence information indicating the occurrence of the biological reaction of the subject E. In other words, in response to the operation performed by the operator, the operation unit 46 inputs the signal serving as the occurrence information on the biological reaction. The operation unit 46 thus functions as an "input unit".

(Outer Appearance Image Acquiring Unit)

The outer appearance image acquiring unit 50 acquires the outer appearance image by photographing the predetermined body part (such as joint part) of the subject E at least at the photographing timing corresponding to the input of the occurrence information on the biological reaction. The photographing may be any one of the still image photographing and the moving image photographing. The outer appearance image acquiring unit 50 includes at least one of a digital camera and a digital video camera depending on a photographing manner thereof.

In the case of the still image photographing, the outer appearance image acquiring unit 50 can be configured to execute the photographing in response to the input of the occurrence information received from the operation unit 46. As an example thereof, the control unit 41 that has received the input of the occurrence information can be configured to control the outer appearance image acquiring unit 50 to perform the photographing.

Further, the control unit 41 that has received the input of the occurrence information can be configured to perform control for outputting alarm information to allow the operator who has recognized the alarm information to input a photographing trigger for the outer appearance image. Note that, the alarm information is, for example, display information output by the display unit 45 or audio information output by an audio output unit (not shown).

The outer appearance image obtained by the still image photographing corresponds to the outer appearance image acquired at the photographing timing corresponding to the input of the occurrence information on the biological reaction.

An arbitrary number of at least one outer appearance image is obtained by such still image photographing. In a case of acquiring at least two outer appearance images, at least one outer appearance image of those that includes a first-photographed one can be selected as the outer appearance image acquired at the photographing timing corresponding to the input of the occurrence information on the biological reaction. The selection processing includes, for example, processing for extracting the outer appearance image acquired during a time determined in advance and processing for extracting the outer appearance images whose number is determined in advance. Further, the outer appearance image that has been photographed since the start of the still image photographing until the photographing is requested to stop can also be used as the outer appearance image acquired at the photographing timing.

In a case of the moving image photographing, the outer appearance image acquiring unit 50 successively inputs a video signal obtained by repeatedly performing the photographing to the console device 40. Each frame obtained by the moving image photographing corresponds to the outer appearance image. Accordingly, a plurality of outer appearance images along time series are obtained.

Operation

An operation of the X-ray CT apparatus 1 according to this embodiment is described. First to fourth operation examples are described below. In the first operation example, the photographing is performed in the time phase corresponding to the occurrence timing of the biological reaction. In the second operation example, the photographing is performed during the predetermined period including the time phase corresponding to the occurrence timing of the biological reaction. In the third operation example, the photographing is performed by increasing the X-ray intensity in the time phase corresponding to the occurrence timing of the biological reaction. In the fourth operation example, the photographing is performed by increasing the X-ray intensity during the predetermined period including the time phase corresponding to the occurrence timing of the biological reaction.

(First Operation Example)

In this operation example, the photographing is performed in the time phase corresponding to the occurrence timing of the biological reaction. In the following, processing for storing the image and the timing information is first described with reference to FIG. 4, and then the photographing based on the stored information is described with reference to FIG. 5. Note that, the former processing and the latter processing can be continuously performed (preliminary photographing and regular photographing) or can be performed on different dates/times.

Figure 4:
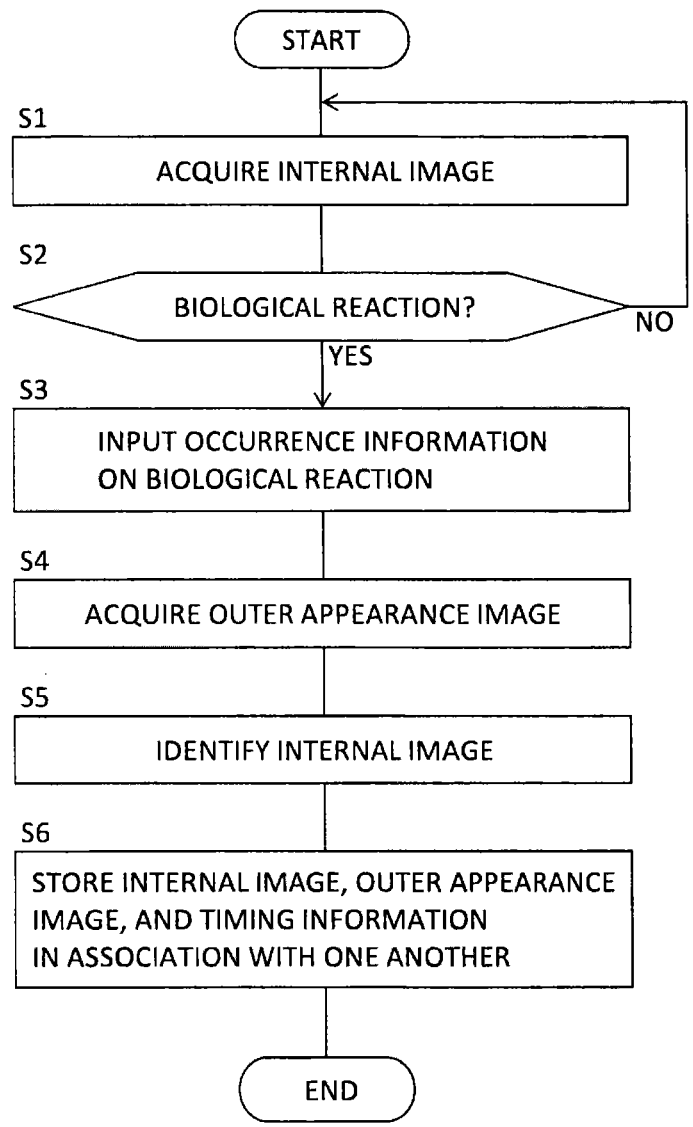
FIG. 4 is a flowchart illustrating a first operation example of the medical image diagnostic apparatus (X-ray CT apparatus) according to the first embodiment.

(Storage of Image and Timing Information: FIG. 4)

(S1: Acquire Internal Image)

The acquisition of the plurality of internal images different in time phase is started. The acquisition of the internal image is continued until at least the input of the occurrence information on the biological reaction (S3). Processing for acquiring the internal image is performed, for example, as follows.

First, the subject E is placed on the top board of the bed apparatus 30 and inserted into the opening portion of the pedestal apparatus 10. When a predetermined scan start operation is performed, the control unit 41 sends a control signal to the scan control unit 42. The scan control unit 42 that has received the control signal controls the high voltage generating unit 14, the pedestal driving unit 15, and the aperture driving unit 17 to scan the range including the predetermined body part of the subject E with X-rays. The X-ray detecting unit 12 detects the X-rays that have passed through the subject E. The data collecting unit 18 collects the detection data successively generated from the X-ray detecting unit 12 along with the progress of the scan. The data collecting unit 18 sends the collected detection data to the pre-processing unit 431. The pre-processing unit 431 performs the above-mentioned pre-processing on the detection data input from the data collecting unit 18 to generate the projection data. The reconstruction processing unit 432 subjects the projection data to the reconstruction processing based on a reconstruction condition set in advance, to thereby form the plurality of internal images different in time phase.

(S2 and S3: Input Occurrence Information on Biological Reaction)

When recognizing the occurrence of a predetermined biological reaction (S2: YES), the operator operates the operation unit 46. The operation unit 46 that has received the operation inputs the signal serving as the occurrence information on the biological reaction to the control unit 41 (S3).

(S4: Acquire Outer Appearance Image)

The control unit 41 that has received the input of the occurrence information on the biological reaction controls the outer appearance image acquiring unit 50 to photograph the predetermined body part of the subject E. Alternatively, the control unit 41 that has received the input of the occurrence information on the biological reaction causes predetermined alarm information to be output. The operator who has recognized the alarm information operates the operation unit 46 to instruct the acquisition of the outer appearance image. In response to the instruction, the outer appearance image acquiring unit 50 performs the photographing. Therefore, the outer appearance image is obtained.

(S5: Identify Internal Image)

The image identifying unit 434 executes any one of the above-mentioned processings, to thereby identify the internal image acquired at substantially the same time as the input of the occurrence information on the biological reaction (S3) among the plurality of internal images acquired in Step S1.

(S6: Store Internal Image, Outer Appearance Image, and Timing Information in Association with One Another)

The control unit 41 stores the internal image identified in Step S5, the outer appearance image acquired in Step S4, and the timing information in the storage unit 44 in association with one another. This is the end of the operation relating to the processing for storing the image and the timing information.

Figure 5:
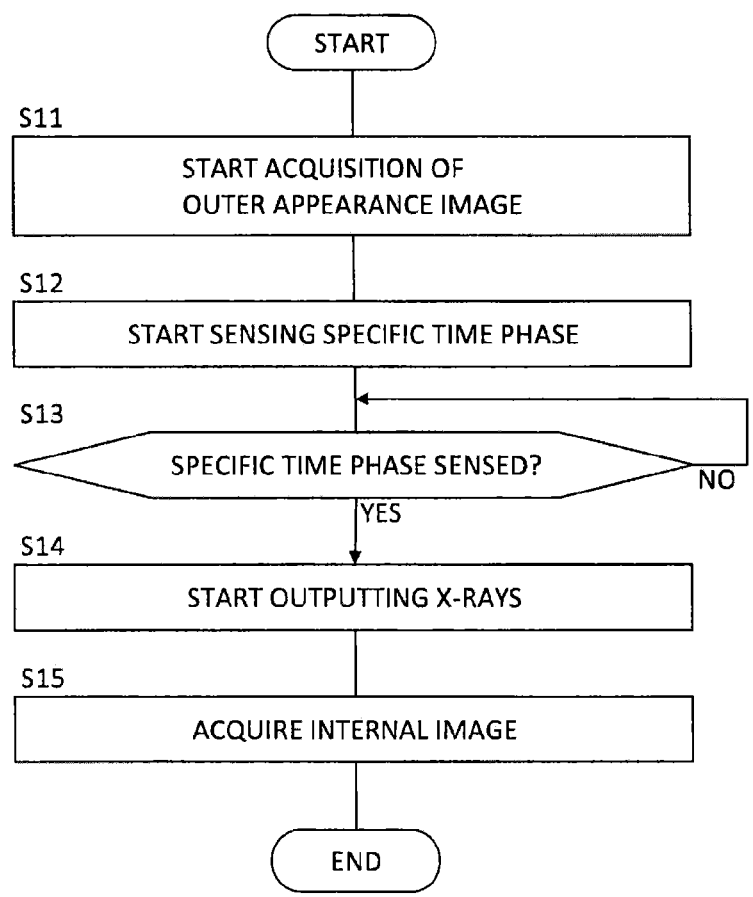
FIG. 5 is a flowchart illustrating the first operation example of the medical image diagnostic apparatus (X-ray CT apparatus) according to the first embodiment.

(Photographing Based on Stored Information: FIG. 5)

(S11: Start Acquisition of Outer Appearance Image)

In response to a predetermined operation for starting the photographing, the outer appearance image acquiring unit 50 starts the acquisition of the outer appearance image of the predetermined body part of the subject E. The predetermined operation may be an operation performed on a photographing start switch of the outer appearance image acquiring unit 50 or may be an operation performed on the operation unit 46 in order to cause the control unit 41 to control the outer appearance image acquiring unit 50 to acquire the outer appearance image. Further, the outer appearance image acquired in this operation example is the images (moving image or a plurality of still images) repeatedly acquired along time series. A repetition rate thereof is determined based on, for example, the speed of the action of the predetermined body part. As a specific example, a relatively low repetition rate is used when the joint is slowly bent, while a relatively high repetition rate is used when the joint is quickly bent.

Note that, along with the start of the acquisition of the outer appearance image, it is possible to control the pedestal driving unit 15 to start rotating the X-ray generating unit 11, the X-ray detecting unit 12, and the like. The X-rays are not output in this stage.

(S12 and S13: Sense Specific Time Phase)

The time phase sensing unit 436 compares each of the outer appearance images (new outer appearance images) repeatedly acquired by the outer appearance image acquiring unit 50 with the outer appearance image stored in the storage unit 44, to thereby sense the arrival of the specific time phase corresponding to the timing information.

(S14: Start Outputting X-Rays)

In response to the fact that the time phase sensing unit 436 has sensed the arrival of the specific time phase, the control unit 41 controls the internal image acquiring unit 100 to start outputting X-rays. Note that, by rotating the X-ray generating unit 11 and the like in advance as described above, CT photographing can be started smoothly.

(S15: Acquire Internal Image)

In response to the start of the outputting of the X-rays performed in Step S14, the internal image acquiring unit 100 starts the acquisition of the internal image. An acquisition time (scan time) for the internal image can be set appropriately based on an exposure dose, a treatment policy, and the like.

The internal image obtained in this operation example is an image that represents the time phase corresponding to the occurrence timing of the biological reaction. Further, according to this operation example, the photographing can be performed at a notable timing, in other words, the occurrence timing of the biological reaction, which can reduce the exposure dose. Further, the photographing can be performed without missing the notable timing.

(Second Operation Example)

Figure 6:
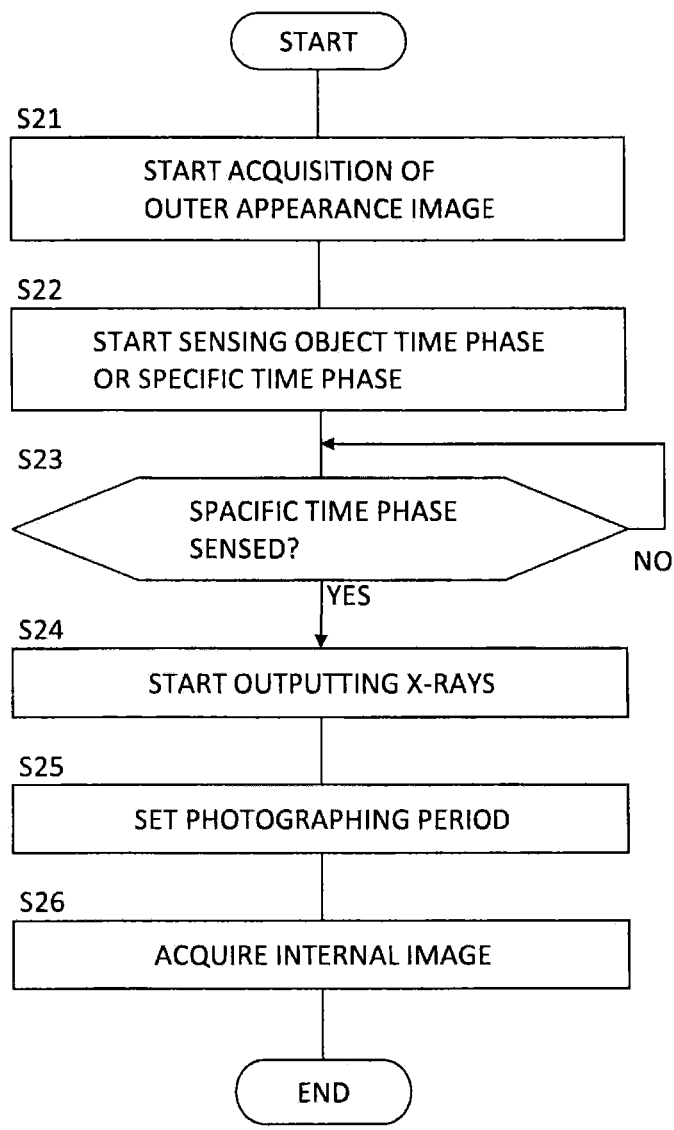
FIG. 6 is a flowchart illustrating a second operation example of the medical image diagnostic apparatus (X-ray CT apparatus) according to the first embodiment.

In this operation example, the photographing is performed during the predetermined period including the time phase corresponding to the occurrence timing of the biological reaction. This operation example also includes the processing for storing the image and the timing information and the photographing based on the stored information, but the former is the same as the first operation example, and hence the description thereof is omitted. An example of the latter is described with reference to FIG. 6.

(S21: Start Acquisition of Outer Appearance Image)

In response to the predetermined operation for starting the photographing, the outer appearance image acquiring unit 50 starts the acquisition of the outer appearance image of the predetermined body part of the subject E. Further, at the start of the acquisition of the outer appearance image, the pedestal driving unit 15 can be controlled to start rotating the X-ray generating unit 11 and the like. The X-rays are not output in this stage. Details of processing of this step are the same as the first operation example.

(S22 and S23: Sense Object Time Phase or Specific Time Phase)

The time phase sensing unit 436 compares each of the outer appearance images (new outer appearance images) repeatedly acquired by the outer appearance image acquiring unit 50 with the outer appearance image stored in the storage unit 44, to thereby sense the arrival of the object time phase included in the predetermined period corresponding to a photographing period or the arrival of the specific time phase corresponding to the timing information. The time phase to be sensed is selected based on the above-mentioned relationship between the specific time phase and the predetermined period.

(S24: Start Outputting X-Rays)

In response to the fact that the time phase sensing unit 436 has sensed the arrival of the object time phase or the specific time phase, the control unit 41 controls the internal image acquiring unit 100 to start outputting X-rays. Note that, by rotating the X-ray generating unit 11 and the like in advance as described above, the CT photographing can be started smoothly.

(S25: Set Photographing Period)

The control unit 41 sets the photographing period in response to the fact that the time phase sensing unit 436 has sensed the object time phase or the specific time phase. This processing is executed by, for example, a timer function of a microprocessor for measuring the time having a length determined in advance. Note that, Steps S24 and S25 are started at substantially the same time. Further, the photographing time can be set appropriately based on the exposure dose, the treatment policy, and the like.

(S26: Acquire Internal Image)

In response to the start of the outputting of the X-rays in Step S24, the internal image acquiring unit 100 starts the acquisition of the internal image. The photographing is continued over the photographing period set in Step S25. In other words, in response to the fact that the photographing time has elapsed, the control unit 41 stops outputting the X-rays.

The internal image obtained in this operation example is an image that represents the action of the predetermined body part performed during the predetermined period including the time phase corresponding to the occurrence timing of the biological reaction. According to this operation example, the photographing can be performed only during the predetermined period including the notable timing, in other words, the occurrence timing of the biological reaction, which can reduce the exposure dose. Further, the photographing can be performed without missing the notable timing.

(Third Operation Example)

Figure 7:
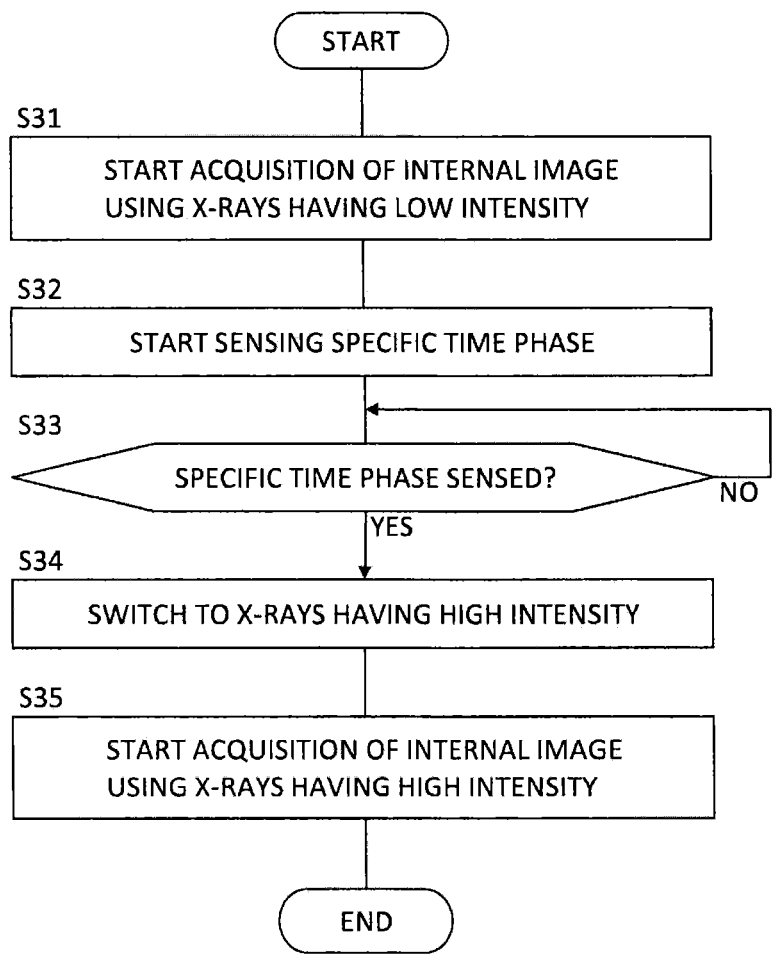
FIG. 7 is a flowchart illustrating a third operation example of the medical image diagnostic apparatus (X-ray CT apparatus) according to the first embodiment.

In this operation example, the photographing is performed by increasing the X-ray intensity in the specific time phase corresponding to the occurrence timing of the biological reaction. This operation example also includes the processing for storing the image with the timing information as well as the photographing based on the stored information, but the former is the same as the first operation example, and hence the description thereof is omitted. An example of the latter is described with reference to FIG. 7. In the following example, the internal image is used to sense the specific time phase, but in the case of acquiring the outer appearance image in parallel with the internal image, the outer appearance image can be used to sense the specific time phase. Further, the first and second intensities of X-rays are assumed to be determined in advance.

(S31: Start Acquisition of Internal Image Using X-Rays having Low Intensity)

When a predetermined instruction to start the photographing is issued, the control unit 41 controls the internal image acquiring unit 100 to start the acquisition of the internal image using X-rays having a low intensity (second intensity). This processing is executed in the same manner as the first operation example.

(S32 and S33: Sense Specific Time Phase)

The time phase sensing unit 436 compares each of the outer appearance images (new outer appearance images) repeatedly acquired by the outer appearance image acquiring unit 50 with the outer appearance image stored in the storage unit 44, to thereby sense the arrival of the specific time phase corresponding to the timing information.

(S34: Switch to X-Rays Having High Intensity)

In response to the fact that the time phase sensing unit 436 has sensed the arrival of the specific time phase, the control unit 41 controls the internal image acquiring unit 100 to switch the intensity of the X-rays output from the X-ray generating unit 11 from the low intensity (second intensity) to a high intensity (first intensity).

(S35: Start Acquisition of Internal Image Using X-Rays Having High Intensity)

In response to the switching of the X-ray intensity performed in Step S34, the internal image acquiring unit 100 starts the acquisition of the internal image using the X-rays having the high intensity. The acquisition time (scan time) for the internal image can be set appropriately based on the exposure dose, the treatment policy, and the like.

In response to the fact that the specific time phase has elapsed, the control unit 41 controls the internal image acquiring unit 100 to switch the X-ray intensity from the high intensity to the low intensity. Alternatively, in response to the fact that the specific time phase has elapsed, the control unit 41 controls the internal image acquiring unit 100 to stop outputting the X-rays.

According to this operation example, a relatively high-definition image is acquired by using the X-rays having the high intensity in the time phase corresponding to the occurrence timing of the biological reaction, while in the other time phases, a relatively low-definition image is acquired by using the X-rays having the low intensity. Therefore, while achieving reduction of the exposure dose, it is possible to acquire a high-definition image at the notable timing, in other words, the occurrence timing of the biological reaction.

(Fourth Operation Example)

Figure 8:
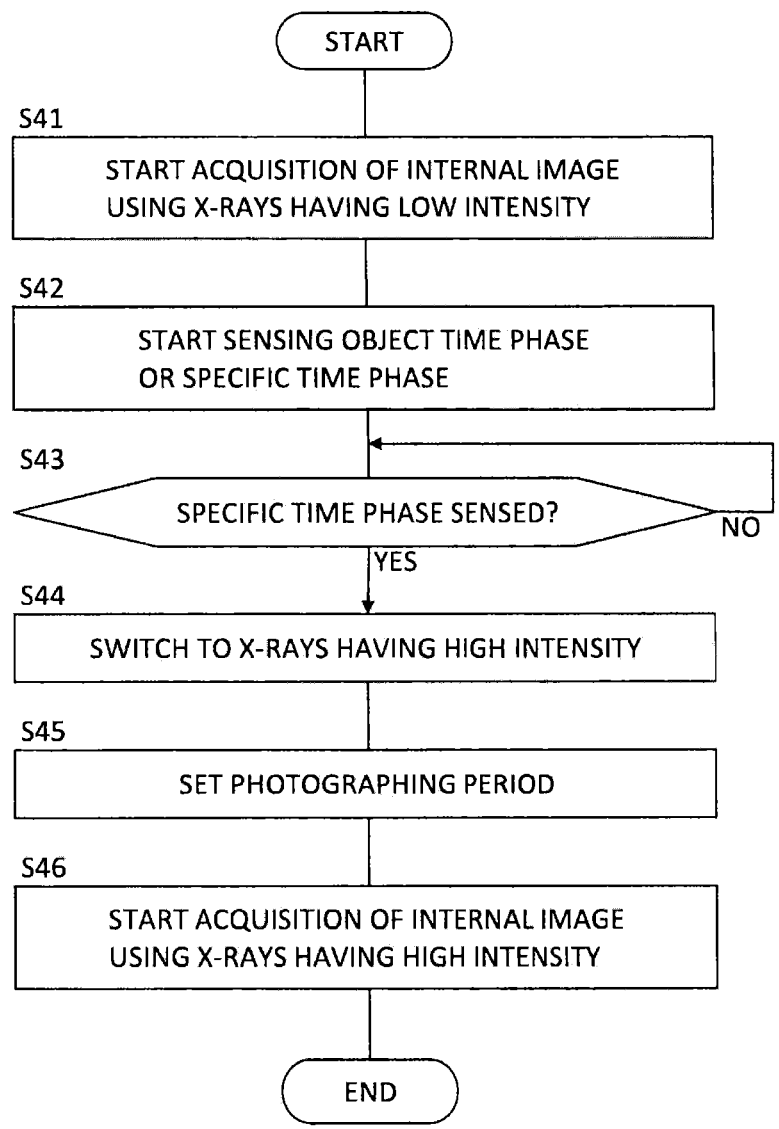
FIG. 8 is a flowchart illustrating a fourth operation example of the medical image diagnostic apparatus (X-ray CT apparatus) according to the first embodiment.

In this operation example, the photographing is performed by increasing the X-ray intensity during the predetermined period including the time phase corresponding to the occurrence timing of the biological reaction. This operation example also includes the processing for storing the image and the timing information and the photographing based on the stored information, but the former is the same as the first operation example, and hence the description thereof is omitted. An example of the latter is described with reference to FIG. 8. In the following example, the internal image is used to sense the specific time phase, but in the case of acquiring the outer appearance image in parallel with the internal image, the outer appearance image can be used to sense the specific time phase. Further, the first and second intensities of X-rays are assumed to be determined in advance.

(S41: Start Acquisition of Internal Image Using X-Rays Having Low Intensity)

When a predetermined instruction to start the photographing is issued, the control unit 41 controls the internal image acquiring unit 100 to start the acquisition of the internal image using X-rays having a low intensity (second intensity). This processing is executed in the same manner as the first operation example.

(S42 and S43: Sense Object Time Phase or Specific Time Phase)

The time phase sensing unit 436 compares each of the outer appearance images (new outer appearance images) repeatedly acquired by the outer appearance image acquiring unit 50 with the outer appearance image stored in the storage unit 44, to thereby sense the arrival of the object time phase included in the predetermined period corresponding to the photographing period or the arrival of the specific time phase corresponding to the timing information. The time phase to be sensed is selected based on the above-mentioned relationship between the specific time phase and the predetermined period.

(S44: Switch to X-Rays Having High Intensity)

In response to the fact that the time phase sensing unit 436 has sensed the object time phase or the specific time phase, the control unit 41 controls the internal image acquiring unit 100 to switch the intensity of the X-rays output from the X-ray generating unit 11 from the low intensity (second intensity) to the high intensity (first intensity).

(S45: Set Photographing Period)

The control unit 41 sets the photographing period in response to the fact that the time phase sensing unit 436 has sensed the object time phase or the specific time phase. This processing is executed in the same manner as the second processing example. Note that, Steps S44 and S45 are started at substantially the same time. Further, the photographing time can be set appropriately based on the exposure dose, the treatment policy, and the like.

(S46: Start Acquisition of Internal Image Using X-Rays Having High Intensity)

In response to the switching of the X-ray intensity performed in Step S44, the internal image acquiring unit 100 starts the acquisition of the internal image using the X-rays having the high intensity. The acquisition time (scan time) for the internal image can be set appropriately based on the exposure dose, the treatment policy, and the like.

In response to the fact that the photographing period has elapsed, the control unit 41 controls the internal image acquiring unit 100 to switch the X-ray intensity from the high intensity to the low intensity. Alternatively, in response to the fact that the photographing period has elapsed, the control unit 41 controls the internal image acquiring unit 100 to stop outputting the X-rays.

According to this operation example, a relatively high-definition image is acquired by using the X-rays having the high intensity in the time phase included in the set photographing period, while in the other time phases, a relatively low-definition image is acquired by using the X-rays having the low intensity. Therefore, while achieving reduction of the exposure dose, it is possible to acquire a high-definition image at the notable timing, in other words, the predetermined period including the occurrence timing of the biological reaction.

Display Mode

A method of displaying the internal image and the outer appearance image stored as described above is described. Display modes described below can also be applied appropriately to a second embodiment.

(First Display Example)

This display example relates to a case where both the internal image and the outer appearance image are displayed.

In response to the reception of a predetermined trigger, the control unit 41 reads the internal image and the outer appearance image that are associated with each other from the storage unit 44, and displays the internal image and the outer appearance image on the display unit 45. In a display mode therefor, only one of the internal image and the outer appearance image that have been read may be displayed, or both thereof may be displayed. The latter includes a case where both the images are displayed side by side and a case where both the images are displayed with one superimposed on the other.

According to the first display example, both the images that are associated with each other can easily be viewed while being compared with each other.

(Second Display Example)

This display example relates to a case where there is a request to display one of the internal image and the outer appearance image. In a case of employing this display example, the operation unit 46 is used to issue an instruction to display one of the internal image and the outer appearance image that are associated with each other.

The control unit 41 displays a screen for designating the image on the display unit 45. This screen presents, for example, at least one piece of information including patient identification information (such as patient's ID and patient name), a photographing date/time, and a reduced image (thumbnail) of the photographed image. The operator uses the operation unit 46 to designate a desired piece of the presented information.

The control unit 41 recognizes a designation result thereof as the instruction to display one of the above-mentioned images, and in response to the instruction, displays the designated image and the image associated therewith (corresponding to the other one of the above-mentioned images) on the display unit 45.

According to the second display example, it is possible to facilitate work for viewing both the images that are associated with each other.

(Third Display Example)

This display example relates to a case of subjecting the internal image to moving image display (including slide show-type display).

The control unit 41 stores the plurality of internal images acquired by the internal image acquiring unit 100 in the storage unit 44. Then, the control unit 41 executes the moving image display by switching and displaying those internal images along time series at predetermined time intervals on the display unit 45.

When performing such moving image display, the control unit 41 displays the information indicating the occurrence of the biological reaction on the display unit 45 at a timing at which the internal image (at least one frame; referred to as "specific frame") identified by the image identifying unit 434 is displayed. The displayed information is referred to as "occurrence timing information". Examples of the occurrence timing information include the character string information or the image information indicating the occurrence of the biological reaction and numerical value information indicating the occurrence timing of the biological reaction or an occurrence period (duration) thereof.

Examples of the timing for displaying the occurrence timing information include the same timing as the displaying of (the first one of) the specific frames, the same timing as the displaying of any one of a plurality of specific frames, and a timing before the displaying of (the first one of) the specific frames. In the case of performing the displaying before the specific frame, it is possible to display information for counting down to the arrival of a display timing for (the first one of) the specific frames. Further, information for counting up with the occurrence of the start of the biological reaction as a trigger or information for counting down to the end of the biological reaction may be displayed.

According to the third display example, it is possible to easily grasp which state the interior of the subject is in when the biological reaction occurs.

(Action/Effects)

Action and effects of the X-ray CT apparatus 1 according to this embodiment are described.

The X-ray CT apparatus 1 includes the internal image acquiring unit 100, the operation unit 46, the outer appearance image acquiring unit 50, the storage unit 44, and the control unit 41. The internal image acquiring unit 100 continuously or intermittently irradiates the predetermined body part of the subject E with X-rays to acquire the plurality of internal images different in time phase. The operation unit 46 is used to input the occurrence information indicating the occurrence of the predetermined biological reaction of the subject E. The outer appearance image acquiring unit 50 acquires the outer appearance image by photographing the predetermined body part of the subject E at least at the photographing timing corresponding to the input of the occurrence information. The control unit 41 stores the outer appearance image acquired at the photographing timing and the timing information indicating the occurrence timing of the biological reaction in the storage unit 44 in association with each other, and stores at least one of the plurality of internal images acquired by the internal image acquiring unit 100 in the storage unit 44.

The X-ray CT apparatus 1 may include the image identifying unit 434. The image identifying unit 434 identifies the internal image acquired at substantially the same time as the input of the occurrence information among the plurality of internal images acquired by the internal image acquiring unit 100. The control unit 41 stores the identified internal image, the outer appearance image acquired at the above-mentioned photographing timing, and the timing information in the storage unit 44 in association with one another.

In a case where the outer appearance image acquiring unit 50 repeatedly photographs the predetermined body part to sequentially acquire the outer appearance images, the image identifying unit 434 may be configured to identify the outer appearance image acquired at substantially the same time as the input of the occurrence information among the sequentially-acquired outer appearance images. The control unit 41 stores the identified outer appearance image as the outer appearance image acquired at the above-mentioned photographing timing in the storage unit 44 in association with the timing information.

The X-ray CT apparatus 1 may include the time phase sensing unit 436. The time phase sensing unit 436 senses the arrival of the specific time phase or the object time phase by comparing the new internal image acquired by applying the X-rays having the second intensity that is relatively low or the new outer appearance image acquired by the outer appearance image acquiring unit 50 with the outer appearance image stored in the storage unit 44. In response to the arrival of the time phase, the control unit 41 acquires the new internal image or switches the X-ray intensity.

According to the X-ray CT apparatus 1 described above, the outer appearance image acquired at the photographing timing corresponding to the input of the occurrence information indicating the occurrence timing of the biological reaction and the timing information indicating the occurrence timing of the biological reaction can be stored in the storage unit 44 in association with each other, and the internal image can also be stored in the storage unit 44. Therefore, the viewer of the image can recognize that the outer appearance image is obtained at the occurrence timing of the biological reaction.

Further, by storing the internal image acquired at substantially the same time as the input of the occurrence information as well in association with the outer appearance image and the timing information, it is possible to recognize that the internal image is obtained at the occurrence timing of the biological reaction. In addition, based on the internal image, the viewer can grasp the internal state at the occurrence timing of the biological reaction, in other words, the action state of the body.

Therefore, according to the X-ray CT apparatus 1, it is possible to grasp the relationship between the action state of the body and the occurrence timing of the biological reaction. For example, in the case of performing the examination of the joint part, the viewer can grasp which state the bones within the joint are in when the pain occurs.

Further, it is possible to reduce the exposure dose by using the outer appearance image stored in the storage unit 44 to perform new photographing.

Second Embodiment

In the first embodiment, the outer appearance image and the timing information are stored in association with each other, while in the second embodiment, the internal image and the timing information are stored in association with each other. In this embodiment, there is no need to provide the outer appearance image acquiring unit.

Configuration

Figure 9:
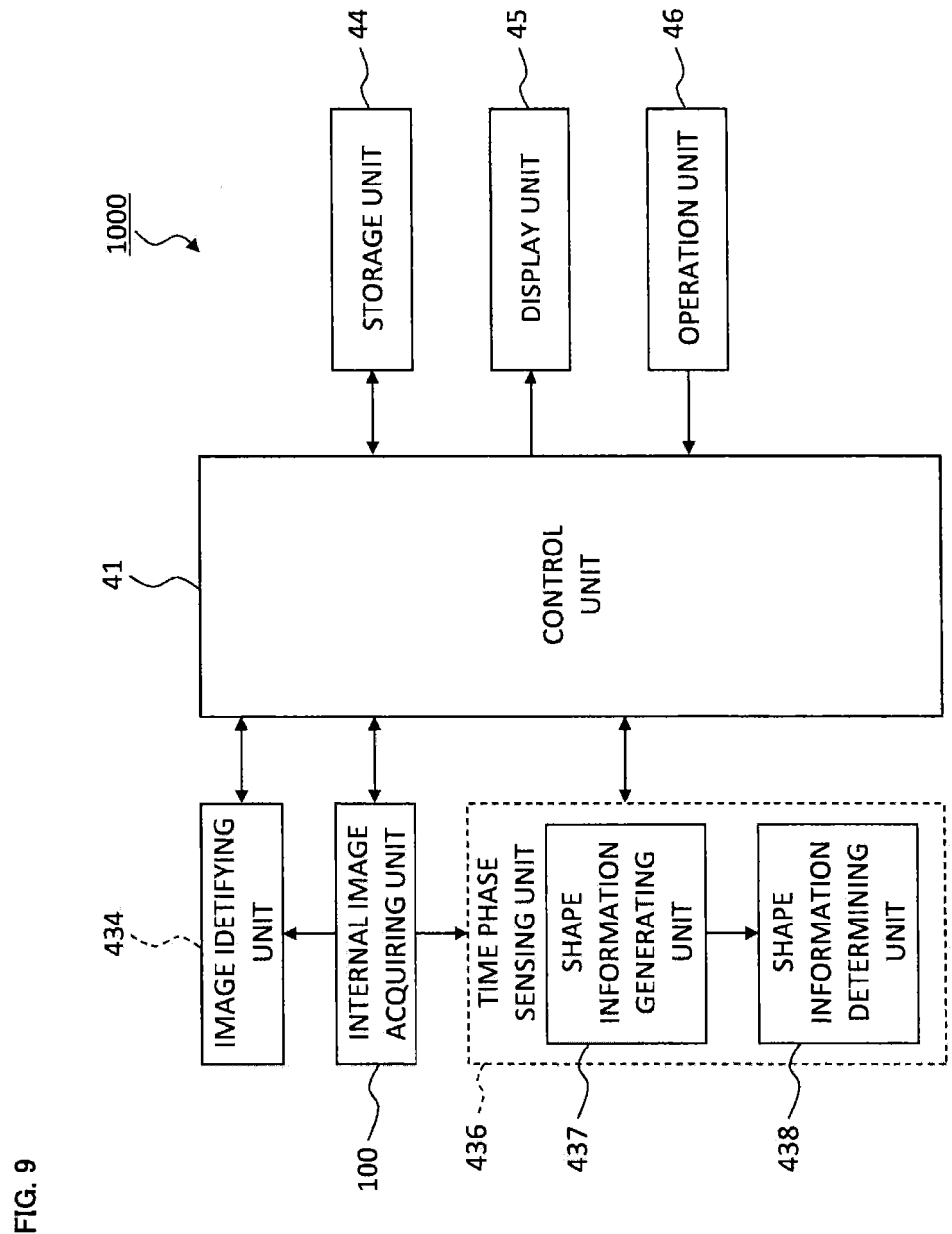
FIG. 9 is a block diagram illustrating a configuration of a medical image diagnostic apparatus (X-ray CT apparatus) according to a second embodiment.

FIG. 9 illustrates a configuration example of a medical image diagnostic apparatus (X-ray CT apparatus) 1000 according to this embodiment. FIG. 9 corresponds to FIG. 2 of the first embodiment. A detailed configuration of the X-ray CT apparatus 1000 conforms to, for example, FIG. 1.

The X-ray CT apparatus 1000 includes the control unit 41, the storage unit 44, the display unit 45, the operation unit 46, the internal image acquiring unit 100, the image identifying unit 434, and the time phase sensing unit 436. The time phase sensing unit 436 includes the shape information generating unit 437 and the shape information determining unit 438. Each of those components has the same configuration and function as the corresponding component in the first embodiment. The X-ray CT apparatus 1000 is now described in consideration of what is described in the first embodiment. The same reference numerals as those of the first embodiment are used.

The internal image acquiring unit 100 continuously or intermittently irradiates the predetermined body part of the subject E with X-rays to acquire the plurality of internal images different in time phase. The operation unit 46 is used to input the occurrence information indicating the occurrence of the predetermined biological reaction of the subject E. The image identifying unit 434 identifies the internal image acquired at substantially the same time as the input of the occurrence information among the plurality of internal images acquired by the internal image acquiring unit 100. The control unit 41 stores the internal image identified by the image identifying unit 434 and the timing information indicating the occurrence timing of the biological reaction in the storage unit 44 in association with each other.

The internal image acquiring unit 100 may be configured to acquire the new internal image based on the internal image and the timing information stored in the storage unit 44. With regard to this case, two processing examples are described.

In a first processing example, based on the internal image and the timing information stored in the storage unit 44, the internal image acquiring unit 100 acquires the new internal image in the specific time phase corresponding to the timing information. The specific time phase has been described in the first embodiment.

Further, in the first processing example, the internal image acquiring unit 100 can acquire the plurality of new internal images by applying the X-rays having the first intensity in the specific time phase and applying the X-rays having the second intensity that is lower than the first intensity in the time phase other than the specific time phase. In other words, the photographing can be performed by using the X-rays having a relatively high intensity in the specific time phase, while in the time phase other than the specific time phase, the photographing can be performed by using the X-rays having a relatively low intensity.

Further, in the first processing example, the time phase sensing unit 436 senses the arrival of the specific time phase by comparing the new internal image acquired by applying the X-rays having the second intensity with the internal image stored in the storage unit 44. Note that, in the first embodiment, the new internal image or the new outer appearance image is compared with the outer appearance image stored in the storage unit 44, but in this embodiment, the internal images are compared with each other. The first and second embodiments are different only in the type of image, and hence the comparison processing according to this embodiment can be executed in the same manner as the first embodiment.

A configuration example of the time phase sensing unit 436 includes the shape information generating unit 437 and the shape information determining unit 438. The shape information generating unit 437 analyzes each of the new internal image acquired by applying the X-rays having the second intensity and the internal image stored in the storage unit 44, and generates the predetermined body part shape information indicating the shape of the predetermined body part of the subject E. The shape information determining unit 438 determines whether or not the predetermined body part shape information generated from the new internal image and the predetermined body part shape information generated from the internal image stored in the storage unit 44 substantially match each other. The time phase sensing unit 436 determines that the specific time phase has arrived when it is determined that the above-mentioned pieces of predetermined body part shape information substantially match each other.

When the time phase sensing unit 436 senses the arrival of the specific time phase, the control unit 41 controls the internal image acquiring unit 100 to switch the intensity of the X-rays output from the X-ray generating unit 11 from the second intensity to the first intensity. This is the end of the description of the first processing example.

In a second processing example, based on the internal image and the timing information stored in the storage unit 44, the internal image acquiring unit 100 acquires the new internal image during the predetermined period including the time phase corresponding to the timing information. The predetermined period has been described in the first embodiment.

Further, in the second operation example, the internal image acquiring unit 100 can acquire the plurality of new internal images by applying the X-rays having the first intensity in the time phase included in the predetermined period and applying the X-rays having the second intensity that is lower than the first intensity in the time phase other than the predetermined period. In other words, the photographing can be performed by using the X-rays having a relatively high intensity in the time phase included in the predetermined period, while in the time phase other than the predetermined period, the photographing can be performed by using the X-rays having a relatively low intensity.

Further, in the second operation example, the time phase sensing unit 436 compares the new internal image acquired by applying the X-rays having the second intensity with the internal image stored in the storage unit 44, to thereby sense the arrival of the time phase included in the predetermined period. This processing and the configuration for execution thereof are the same as those of the first embodiment and the above-mentioned first processing example. When the time phase sensing unit 436 senses the arrival of the time phase included in the predetermined period, the control unit 41 controls the internal image acquiring unit 100 to switch the intensity of the X-rays output from the X-ray generating unit 11 from the second intensity to the first intensity. This is the end of the description of the second processing example.

The image identifying unit 434 is described. In the first embodiment, the description has been made of the three processing examples, two of which use the outer appearance image (analysis unit 435). In this embodiment, the outer appearance image is not used, and hence those two processing examples cannot be applied thereto. Note that, in a case where the outer appearance image acquiring unit is added to the configuration of this embodiment, all the three processing examples can be applied in the same manner as the first embodiment.

The first input timing information indicating an input timing for the occurrence information using the operation unit 46 and the second input timing information indicating the timing at which the internal image is acquired by the internal image acquiring unit 100 are input to the image identifying unit 434. The image identifying unit 434 identifies the internal image corresponding to the second input timing information received at substantially the same time as the first input timing information. In other words, the image identifying unit 434 monitors both the input timing for the occurrence information and the acquisition timing for the internal image, and identifies the internal image acquired at a timing that substantially match with the input timing. The identified internal image is set as the internal image acquired at substantially the same time as the input of the occurrence information among the plurality of internal images acquired by the internal image acquiring unit 100.

Operation

An operation of the X-ray CT apparatus 1000 according to this embodiment is described. First and second operation examples are described below. In the first operation example, the photographing is performed by increasing the X-ray intensity in the time phase corresponding to the occurrence timing of the biological reaction. In the second operation example, the photographing is performed by increasing the X-ray intensity during the predetermined period including the time phase corresponding to the occurrence timing of the biological reaction.

(First Operation Example)

In this operation example, the photographing is performed by increasing the X-ray intensity in the time phase corresponding to the occurrence timing of the biological reaction. In the following, processing for storing the internal image and the timing information is first described with reference to FIG. 10, and then the photographing based on the stored information is described with reference to FIG. 11. Note that, the former processing and the latter processing can be continuously performed (preliminary photographing and regular photographing) or can be performed on different dates/times.

Figure 10:
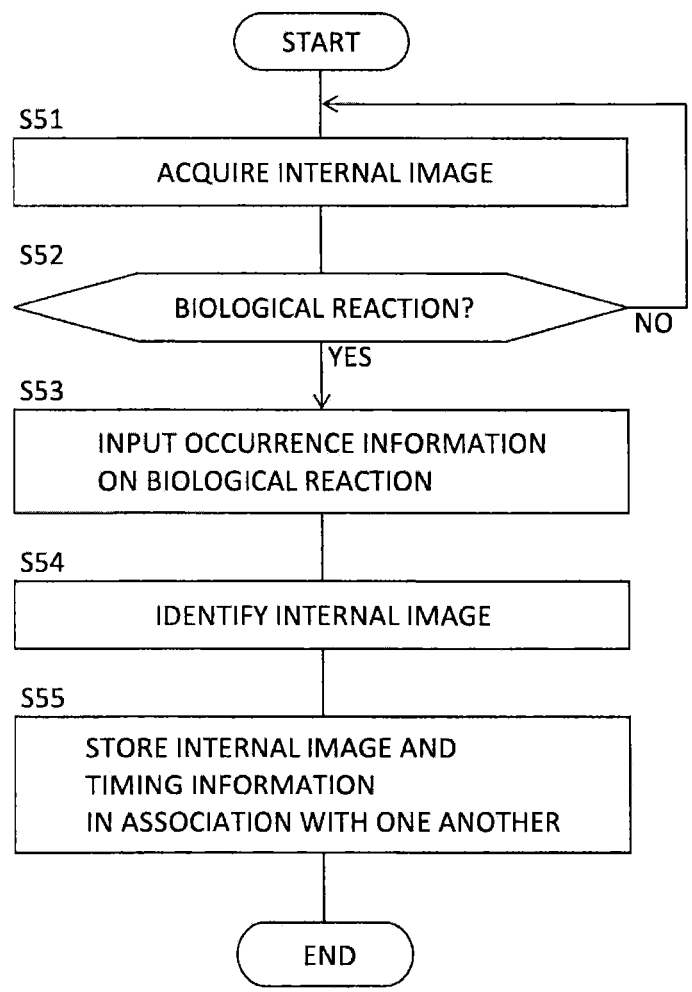
FIG. 10 is a flowchart illustrating a first operation example of the medical image diagnostic apparatus (X-ray CT apparatus) according to the second embodiment.

(Storage of Internal Image and Timing Information: FIG. 10)

(S51: Acquire Internal Image)

The acquisition of the plurality of internal images different in time phase is started. The acquisition of the internal image is continued until at least the input of the occurrence information on the biological reaction (S53). Processing for acquiring the internal image is performed in the same manner as the first embodiment.

(S52 and S53: Input Occurrence Information on Biological Reaction)

When recognizing the occurrence of a predetermined biological reaction (S52: YES), the operator operates the operation unit 46. The operation unit 46 that has received the operation inputs the signal serving as the occurrence information on the biological reaction to the control unit 41 (S53).

(S54: Identify Internal Image)

It is assumed that the first input timing information indicating the input timing for the occurrence information and the second input timing information indicating the timing at which the internal image is acquired by the internal image acquiring unit 100 are input to the image identifying unit 434. The image identifying unit 434 identifies the internal image corresponding to the second input timing information received at substantially the same time as the first input timing information corresponding to Step S53.

(S55: Store Internal Image and Timing Information in Association with each Another)

The control unit 41 stores the internal image identified in Step S54 and the timing information in the storage unit 44 in association with each another. This is the end of the operation relating to the processing for storing the image and the timing information.

Figure 11:
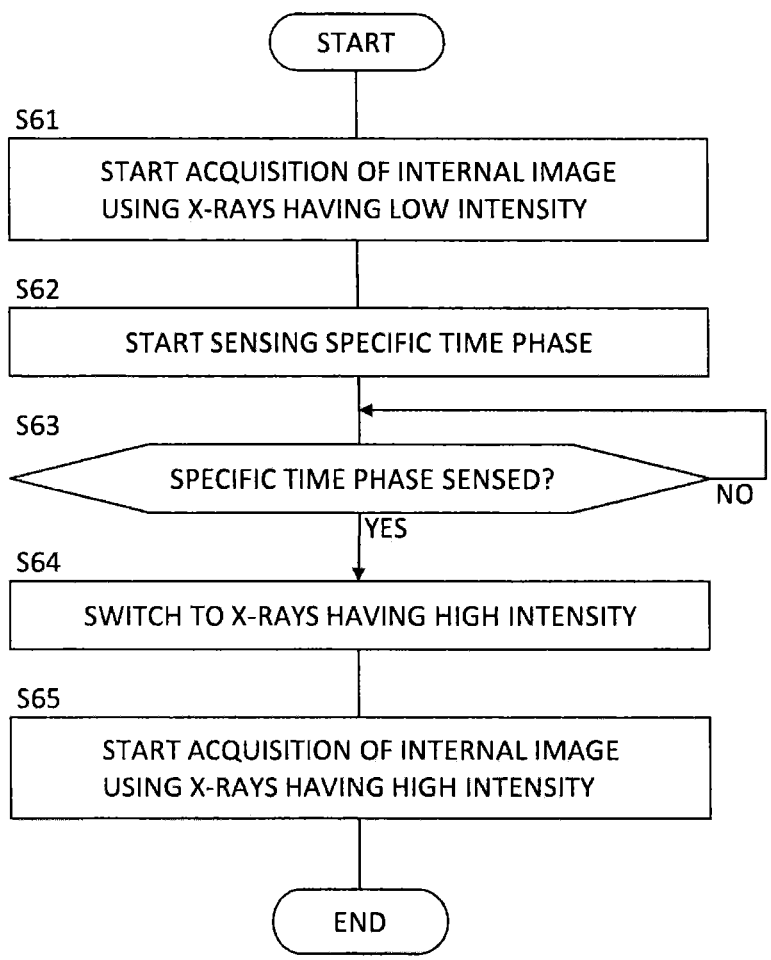
FIG. 11 is a flowchart illustrating the first operation example of the medical image diagnostic apparatus (X-ray CT apparatus) according to the second embodiment.

(Photographing Based on Stored Information: FIG. 11)

(S61: Start Acquisition of Internal Image Using X-Rays Having Low Intensity)

When a predetermined instruction to start the photographing is issued, the control unit 41 controls the internal image acquiring unit 100 to start the acquisition of the internal image using X-rays having a low intensity (second intensity). This processing is executed in the same manner as the first embodiment. Note that, the first and second intensities of X-rays are assumed to be determined in advance.

(S62 and S63: Sense Specific Time Phase)

The time phase sensing unit 436 compares each of the internal images (new internal images) repeatedly acquired by using the X-rays having the low intensity with the internal image stored in the storage unit 44, to thereby sense the arrival of the specific time phase corresponding to the timing information.

(S64: Switch to X-Rays Having High Intensity)

In response to the fact that the time phase sensing unit 436 has sensed the arrival of the specific time phase, the control unit 41 controls the internal image acquiring unit 100 to switch the intensity of the X-rays output from the X-ray generating unit 11 from the low intensity (second intensity) to the high intensity (first intensity).

(S65: Start Acquisition of Internal Image Using X-Rays Having High Intensity)

In response to the switching of the X-ray intensity performed in Step S64, the internal image acquiring unit 100 starts the acquisition of the internal image using the X-rays having the high intensity. The acquisition time (scan time) for the internal image can be set appropriately based on the exposure dose, the treatment policy, and the like.

In response to the fact that the specific time phase has elapsed, the control unit 41 controls the internal image acquiring unit 100 to switch the X-ray intensity from the high intensity to the low intensity. Alternatively, in response to the fact that the specific time phase has elapsed, the control unit 41 controls the internal image acquiring unit 100 to stop outputting the X-rays.

According to this operation example, a relatively high-definition image is acquired by using the X-rays having the high intensity in the time phase corresponding to the occurrence timing of the biological reaction, while in the other time phases, a relatively low-definition image is acquired by using the X-rays having the low intensity. Therefore, while achieving reduction of the exposure dose, it is possible to acquire a high-definition image at the notable timing, in other words, the occurrence timing of the biological reaction.

(Second Operation Example)

Figure 12:
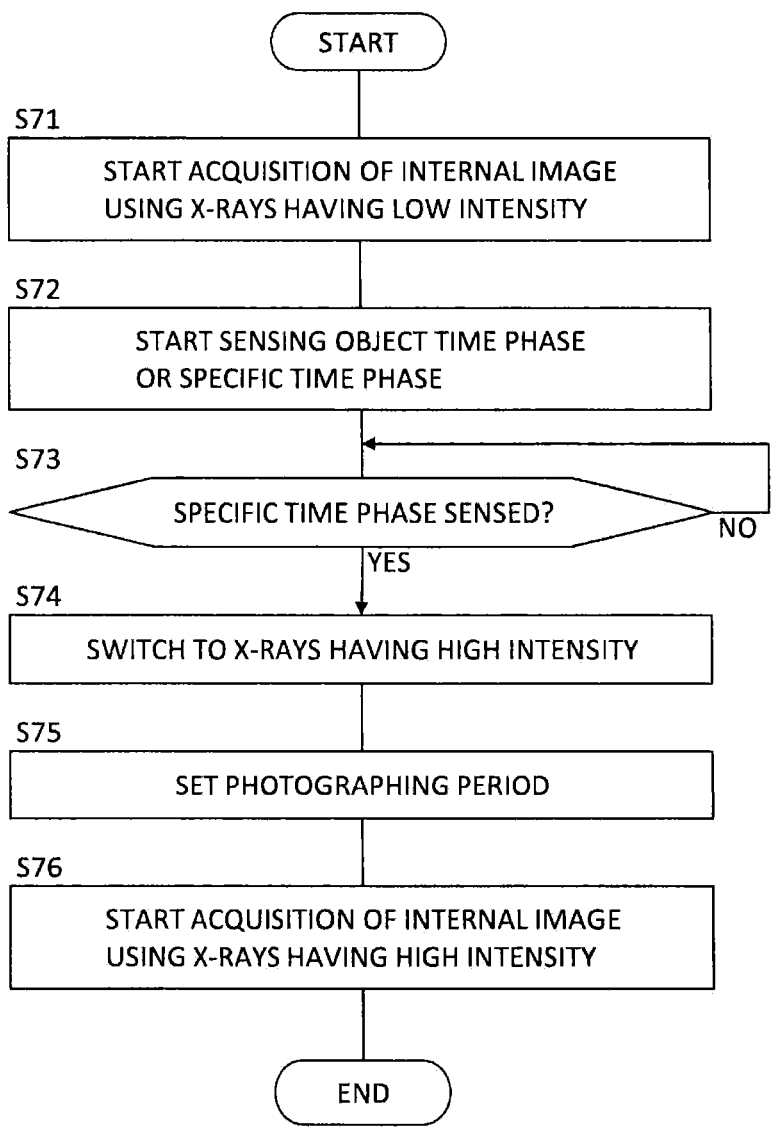
FIG. 12 is a flowchart illustrating a second operation example of the medical image diagnostic apparatus (X-ray CT apparatus) according to the second embodiment.

In this operation example, the photographing is performed by increasing the X-ray intensity during the predetermined period including the time phase corresponding to the occurrence timing of the biological reaction. This operation example also includes the processing for storing the image and the timing information and the photographing based on the stored information, but the former is the same as the first operation example, and hence the description thereof is omitted. An example of the latter is described with reference to FIG. 12. Note that, the first and second intensities of X-rays are assumed to be determined in advance.

(S71: Start Acquisition of Internal Image Using X-Rays Having Low Intensity)

When a predetermined instruction to start the photographing is issued, the control unit 41 controls the internal image acquiring unit 100 to start the acquisition of the internal image using X-rays having the low intensity (second intensity). This processing is executed in the same manner as the first operation example.

(S72 and S73: Sense Object Time Phase or Specific Time Phase)

The time phase sensing unit 436 compares each of the internal images (new internal images) repeatedly acquired by using the X-rays having the low intensity with the internal image stored in the storage unit 44, to thereby sense the arrival of the object time phase included in the predetermined period corresponding to the photographing period or the arrival of the specific time phase corresponding to the timing information. The time phase to be sensed is selected based on the relationship between the specific time phase and the predetermined period, which has been described in the first embodiment.

(S74: Switch to X-Rays Having High Intensity)

In response to the fact that the time phase sensing unit 436 has sensed the object time phase or the specific time phase, the control unit 41 controls the internal image acquiring unit 100 to switch the intensity of the X-rays output from the X-ray generating unit 11 from the low intensity (second intensity) to the high intensity (first intensity).

(S75: Set Photographing Period)

The control unit 41 sets the photographing period in response to the fact that the time phase sensing unit 436 has sensed the object time phase or the specific time phase. This processing is executed in the same manner as the first embodiment. Note that, Steps S74 and S75 are started at substantially the same time. Further, the photographing time can be set appropriately based on the exposure dose, the treatment policy, and the like.

(S76: Start Acquisition of Internal Image Using X-Rays Having High Intensity)

In response to the switching of the X-ray intensity performed in Step S74, the internal image acquiring unit 100 starts the acquisition of the internal image using the X-rays having the high intensity. The acquisition time (scan time) for the internal image can be set appropriately based on the exposure dose, the treatment policy, and the like.

In response to the fact that the photographing period has elapsed, the control unit 41 controls the internal image acquiring unit 100 to switch the X-ray intensity from the high intensity to the low intensity. Alternatively, in response to the fact that the photographing period has elapsed, the control unit 41 controls the internal image acquiring unit 100 to stop outputting the X-rays.

According to this operation example, a relatively high-definition image is acquired by using the X-rays having the high intensity in the time phase included in the set photographing period, while in the other time phases, a relatively low-definition image is acquired by using the X-rays having the low intensity. Therefore, while achieving reduction of the exposure dose, it is possible to acquire a high-definition image at the notable timing, in other words, the predetermined period including the occurrence timing of the biological reaction.

(Action/Effects)

According to the X-ray CT apparatus 1000 of this embodiment, it is possible to store the internal image acquired at substantially the same time as the occurrence of the biological reaction and the timing information indicating the occurrence timing of the biological reaction in association with each other. Therefore, the viewer of the image can recognize that the internal image is obtained at the occurrence timing of the biological reaction. In addition, based on the internal image, the viewer can grasp the internal state at the occurrence timing of the biological reaction, in other words, the action state of the body. Therefore, according to the X-ray CT apparatus 1000, it is possible to grasp the relationship between the action state of the body and the occurrence timing of the biological reaction.

Further, it is possible to reduce the exposure dose by using the internal image stored in the storage unit 44 to perform new photographing.

(Modified Example)

A description is made of a medical image diagnostic apparatus according to a modified example of the embodiments. The contents described above in the embodiments can be arbitrarily combined with each of the modified examples. Further, the modified examples can be combined with one another. In the following, the same components as those of the above-mentioned embodiments are denoted by the same reference numerals in the description.

In this modified example, the state of the subject E is monitored to automatically sense the occurrence of the biological reaction. The medical image diagnostic apparatus according to this modified example is described by particularly focusing on the sensor unit 200 in the embodiment described with reference to FIGS. 1 and 2.

The sensor unit 200 monitors the state of the subject E and senses the occurrence of the biological reaction, to thereby input the signal serving as the occurrence information on the biological information. Examples of the biological information to be input include the utterance, the facial expression, the respiration, the perspiration, the electrocardiogram, the blood pressure, the electromyogram, the electroencephalogram, and the pupil diameter. The biological reaction to be sensed is, for example, a change in the biological information accompanied by the pain. Such a biological reaction is known.

The utterance can be sensed by using a microphone. Examples of contents sensed at this time include contents of the utterance and a voice volume.

The contents of the utterance can be sensed by, for example, the microprocessor (not shown) provided to the sensor unit 200 executing a known speech recognition technology. The microprocessor analyzes an electric signal output from the microphone to determine whether or not a content stored in advance has been uttered. When it is determined that the content has been uttered, the microprocessor inputs an occurrence signal to the control unit 41.

The voice volume can be sensed by, for example, the microprocessor (not shown) provided to the sensor unit 200 analyzing the electric signal output from the microphone. The microprocessor determines based on the electric signal whether or not a volume thereof is equal to or larger than a predetermined threshold value. When it is determined that the volume is equal to or larger than the threshold value, the microprocessor inputs the occurrence signal to the control unit 41.

The facial expression and the pupil diameter can be sensed by photographing a face and an eye of the patient and analyzing the photographed images.

The facial expression can be sensed by the microprocessor (not shown) provided to the sensor unit 200 identifying feature points of the facial expression (for example, points indicating characteristic changes of muscles of facial expression accompanied by the occurrence of the pain) stored in advance by analyzing the photographic image and determining whether or not the positional relationship between those feature points matches the positional relationship corresponding to the biological reaction. When it is determined that the positional relationship between those feature points matches the positional relationship corresponding to the biological reaction, the microprocessor inputs the occurrence signal to the control unit 41.

The pupil diameter can be sensed by the microprocessor (not shown) provided to the sensor unit 200 analyzing the photographed image to extract the image area (eye area) corresponding to the eye, analyzing the eye area to identify the image area (pupil area) corresponding to the pupil, and calculating a diameter of the pupil area. The microprocessor determines whether or not the pupil diameter is within a predetermined allowable range. When it is determined that the pupil diameter is out of the predetermined allowable range, the microprocessor inputs the occurrence signal to the control unit 41.

The respiration, the perspiration, the electrocardiogram, the blood pressure, the electromyogram, and the electroencephalogram can be sensed by using publicly-known devices, in other words, a respiration monitoring device, a perspiration monitoring device, an electrocardiograph, a sphygmomanometer, an electromyograph, and an electroencephalograph, respectively. The electric signal indicating detection results obtained by those devices is input to the microprocessor (not shown) provided to the sensor unit 200. The microprocessor determines whether or not the biological reaction has occurred by comparing the detection results with a predetermined threshold value. When it is determined that the biological reaction has occurred, the microprocessor inputs the occurrence signal to the control unit 41.

The sensor unit 200 may be configured to be able to sense not only the occurrence of the biological reaction but also a degree of the biological reaction. Examples of the degree of the biological reaction include a voice volume, a deformation degree of a facial expression, a rate of respiration, an amount of perspiration, a heart rate, a blood pressure value, a muscle tone, an electroencephalogram frequency, a magnitude of a pupil diameter, and a blinking rate. Information (degree information) indicating those degrees of the biological reactions, which is included in a signal serving as biological reaction information, is input to the control unit 41.

The medical image diagnostic apparatus that has received an input of the occurrence signal from the sensor unit 200 identifies at least one of the internal image and the outer appearance image acquired at substantially the same time as the input timing thereof. Further, in response to the input of the occurrence signal received from the sensor unit 200, it is possible to change a manner in which at least one of the internal image and the outer appearance image is acquired. For example, in response to the input of the occurrence signal received from the sensor unit 200, it is possible to start acquiring at least one of the internal image and the outer appearance image or switching the X-ray intensity.

According to the medical image diagnostic apparatus according to this modified example, in the same manner as the above-mentioned embodiments, it is possible to grasp the relationship between the action state of the body and the occurrence timing of the biological reaction. In addition, the occurrence of the biological reaction can be automatically sensed, which does not bother the user.

Operation

An operation of the operation the X-ray CT apparatus 1 according to this modified example is described. First to seventh operation examples are described below. The first operation example describes control for starting/stopping scanning in response to the input of the biological reaction information. The second operation describes control for changing the irradiation interval (scan condition) of the X-rays in response to the input of the biological reaction information. The third operation describes control for changing a tube current value (scan condition) in response to the input of the biological reaction information. The fourth operation describes control for changing the cross-section interval (reconstruction condition) in response to the input of the biological reaction information. The fifth operation describes control for appending the supplementary information to the image data in response to the input of the biological reaction information. The sixth operation describes control for embedding the embedded information in the image data in response to the input of the biological reaction information. The seventh operation describes control for adding to the image data the additional information that differs depending on the degree information on the biological reaction. At least any two of the first to seventh operation examples may be combined with each other.

(First Operation Example)

Figure 13:
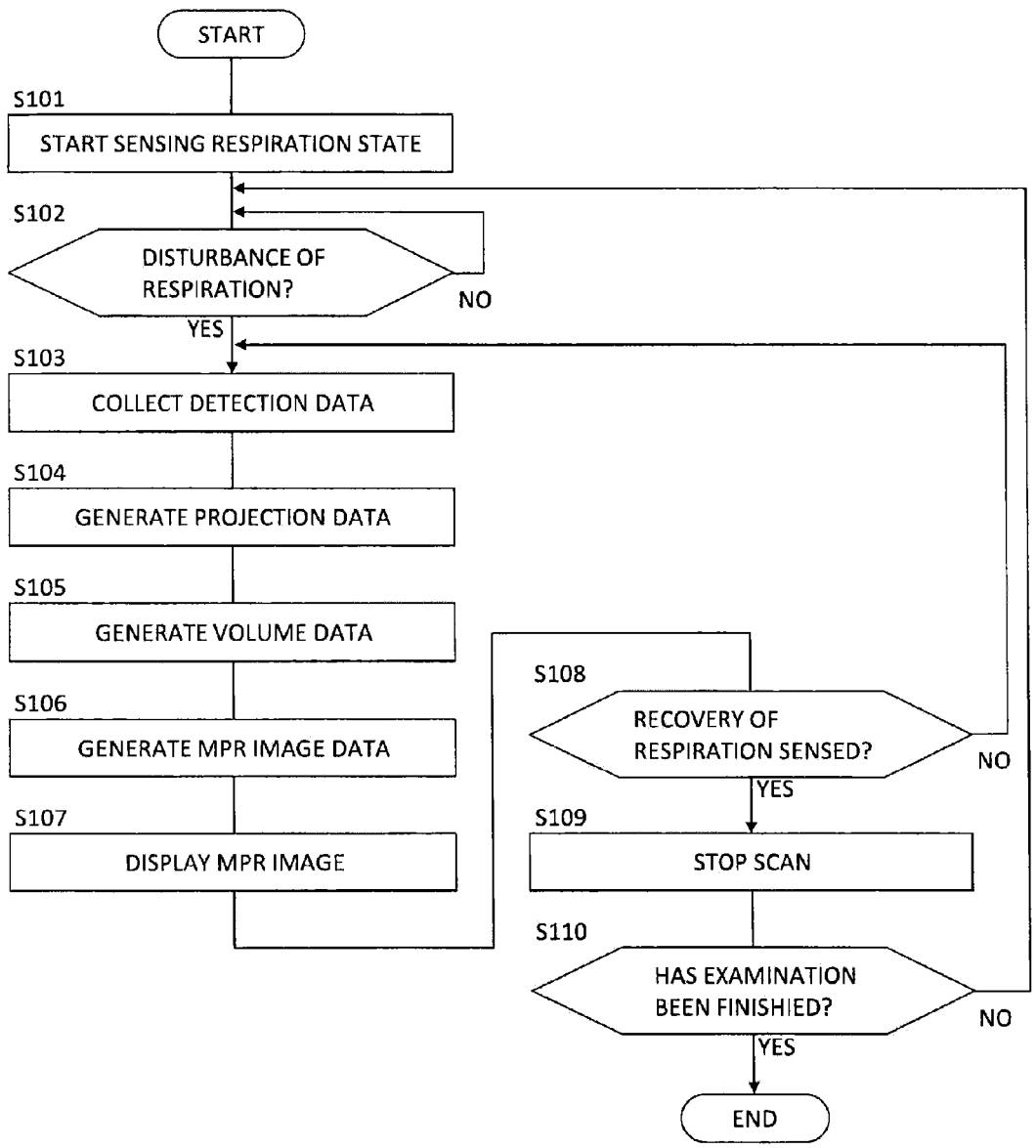
FIG. 13 is a flowchart illustrating a first operation example of an X-ray CT apparatus according to a modified example.

The first operation example relates to control for starting/stopping scanning in response to the input of the biological reaction information. In the following, a description is made of an example of the application to an examination in which the scan is repeatedly performed in a state in which the respiration is disturbed. Note that, it is assumed that preparations for the examination have already been made. In other words, it is assumed that the subject E has been placed on the bed apparatus 30 and inserted into the opening portion of the pedestal apparatus 10 and that the sensor unit 200 (respiration monitoring device) has been attached to the subject E. FIG. 13 illustrates a flow of the first operation example.

(S101: Start Sensing Respiration State)

The sensor unit 200 starts sensing a respiration state of the subject E. It is assumed that the subject E is breathing as usual in this stage. The sensor unit 200 forms a waveform from the signal indicating the sensed respiration state. In a case where the respiration of the subject E is in a normal state, the formed waveform maintains a constant steady state, but when the subject E senses a pain and the respiration changes to disturb the respiration of the subject E, the waveform in the steady state becomes an instable form. The sensor unit 200 stores the waveform in the case where the respiration is in a normal state and the value based on the waveform. The sensor unit 200 senses that the respiration of the subject E is disturbed when an exceptional waveform or value occurs in comparison with the stored data and when, for example, a difference from a normal value exceeds a threshold value.

(S102: Sense Disturbance of Respiration)

When sensing a disturbance of the respiration of the subject E, the sensor unit 200 inputs the biological reaction information (respiration state information) indicating the disturbance to the main control unit 411 (S102: YES).

(S103: Collect Detection Data)

The main control unit 411 that has received the respiration state information sends the control signal to the collection control unit 412. The collection control unit 412 controls the scan control unit 42 to start an X-ray scan for the subject E. The X-ray detecting unit 12 detects the X-rays that have passed through the subject E. The data collecting unit 18 collects the detection data generated from the X-ray detecting unit 12 sequentially along with the scan. The data collecting unit 18 sends the collected detection data to the pre-processing unit 431.

(S104: Generate Projection Data)

The pre-processing unit 431 generates the projection data by subjecting the detection data received from the data collecting unit 18 to the above-mentioned pre-processing.

(S105: Generate Volume Data)

The reconstruction processing unit 432 generates the volume data by subjecting the projection data to the reconstruction processing.

(S106: Generate MPR Image Data)

The rendering processing unit 433 generates MPR image data based on the volume data. The MPR image data may be the image data on any one of orthogonal three-axis images, or may be the image data on the oblique image based on the cross-section that is arbitrarily set.

(S107: Display MPR Image)

The display control unit 413 displays the image (MPR image) based on the generated MPR image data on the display unit 45. The display mode for the MPR image may be any one of a moving image display and a still image display. In this operation example, it is assumed that the moving image display is performed by repeatedly performing the scan while the respiration is disturbed (S108: NO).

(S108: Sense Recovery of Respiration)

When sensing the recovery of the respiration of the subject E, the sensor unit 200 inputs the biological reaction information (respiration state information) indicating the recovery to the main control unit 411 (S108: YES).

(S109: Stop Scan)

The main control unit 411 that has received the respiration state information sends the control signal to the collection control unit 412. The collection control unit 412 controls the scan control unit 42 to stop the X-ray scan for the subject E. This control may be performed to stop all operations of the components relating to the scan or to stop only a part of operations thereof. As an example of the latter, it is possible to cause the high voltage generating unit 14 to stop power supply to the X-ray generating unit 11 while continuing a rotation action of the rotary member 13 caused by the pedestal driving unit 15.

(S110: Has Examination been Finished?)

The main control unit 411 repeatedly executes the operation of Steps S102 to S109 until the examination is finished (S110: YES).

According to this operation example, the scan operation can be automatically controlled based on the respiration state of the subject E. In other words, it is possible to acquire the image by performing the scan when the respiration of the subject E is disturbed and to stop the scan when the respiration is recovered. Accordingly, it is possible to reliably acquire the image in the state in which the respiration is disturbed and to suppress an unnecessary X-ray exposure.

In addition, there is no need to verify the respiration state to perform an operation for starting/stopping scanning. Note that, this operation example has described the case of generating the volume data, but the tomographic image data of a given cross-section may be generated without generating the volume data. Further, without sensing the recovery of the respiration, the scan may be performed only for a predetermined period after sensing the disturbance of the respiration.

(Second Operation Example)

Figure 14:
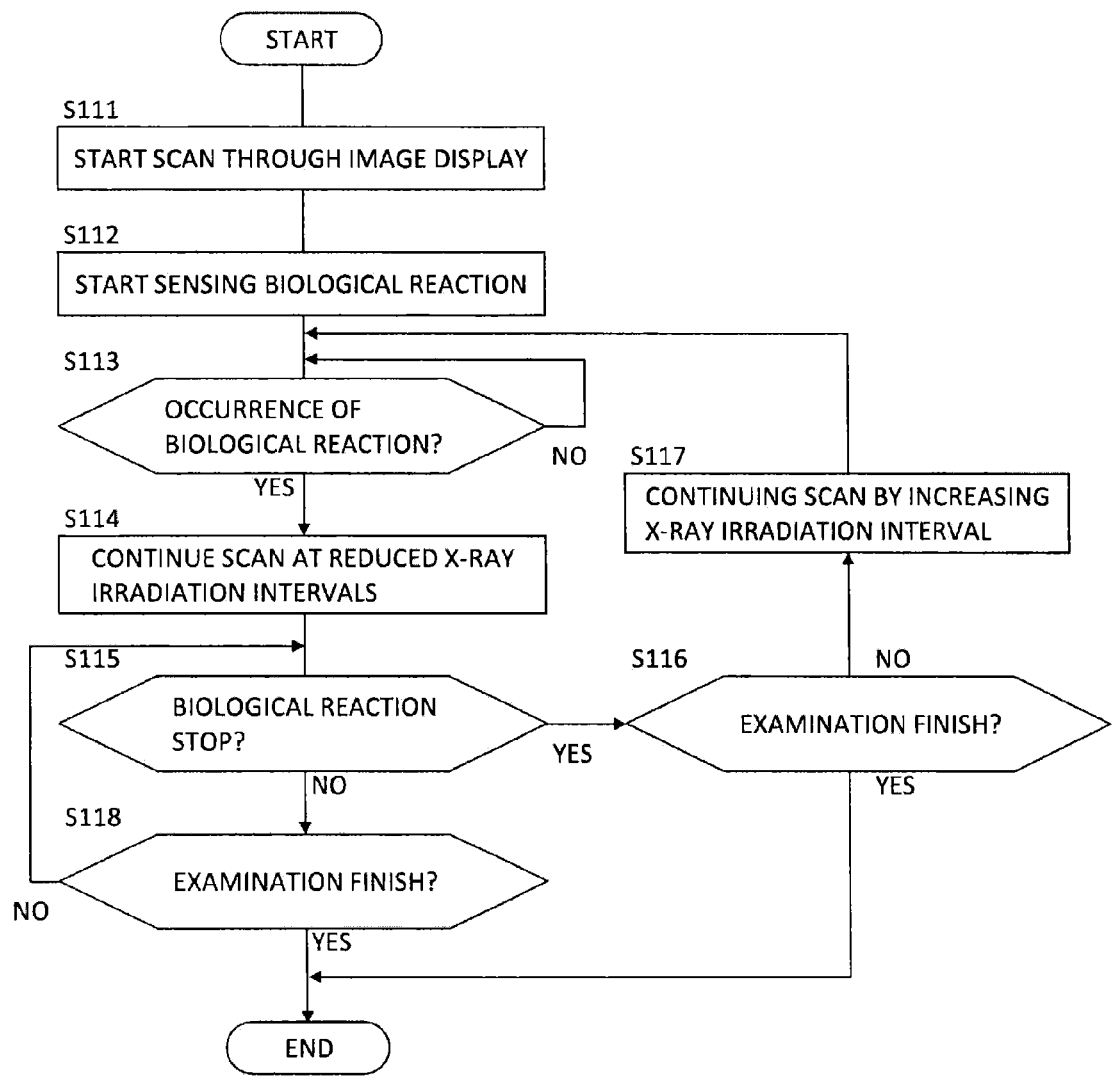
FIG. 14 is a flowchart illustrating a second operation example of the X-ray CT apparatus according to the modified example.

The second operation relates to control for changing the irradiation interval (scan condition) of the X-rays in response to the input of the biological reaction information. FIG. 14 illustrates a flow of the second operation example. Note that, the same operation as the first operation example is only described in brief.

(S111: Start Scan through Image Display)

When a predetermined instruction to start the scan is input, the main control unit 411 executes the processing of Steps S103 to S107 illustrated in FIG. 13. In other words, the main control unit 411 starts the scan, generation of the projection data, generation of the volume data, generation of the MPR image data, and display of the MPR image. Note that, in the scan in this stage, it is assumed that the subject E is irradiated with the X-rays at first irradiation intervals. The first irradiation interval, which is set relatively long, is employed in a case where the biological reaction is not occurring.

(S112: Start Sensing Biological Reaction)

The sensor unit 200 starts sensing the biological reaction of the subject E.

(S113: Sense Occurrence of Biological Reaction)

When sensing the occurrence of the biological reaction, the sensor unit 200 inputs the biological reaction information indicating the occurrence to the main control unit 411 (S113: YES).

(S114: Continue Scan at Reduced X-Ray Irradiation Intervals)

The main control unit 411 that has received the biological reaction information sends the control signal to the collection control unit 412. The collection control unit 412 generates the control signal for switching an X-ray irradiation interval to a second irradiation interval, and sends the control signal to the scan control unit 42. The scan control unit 42 continues the scan by controlling the high voltage generating unit 14 to switch the X-ray irradiation interval from the first irradiation interval to the second irradiation interval. It is assumed that the second irradiation interval is shorter than the first irradiation interval. In other words, the X-ray irradiation interval is reduced in Step S114. Note that, the first irradiation interval and the second irradiation interval are values set in advance.

(S115 to S117: Processing that Accompanies Stopping of Biological Reaction)

When sensing the stopping of the biological reaction, the sensor unit 200 inputs the biological reaction information indicating the stopping to the main control unit 411 (S115: YES). When an instruction to finish the examination is issued (S116: YES), the processing of this operation example is brought to an end. On the other hand, when the instruction to finish the examination is not issued in this stage (S116: NO), the main control unit 411 sends the control signal to the collection control unit 412. The collection control unit 412 generates the control signal for switching the X-ray irradiation interval to the first irradiation interval, and sends the control signal to the scan control unit 42. The scan control unit 42 continues the scan by controlling the high voltage generating unit 14 to switch the X-ray irradiation interval from the second irradiation interval to the first irradiation interval (S117).

(S115 and S118: Processing in Case where Biological Reaction is Continuing)

When the stopping of the biological reaction is not sensed in Step S115, in other words, when the biological reaction is continuing (S115: NO), when the instruction to finish the examination is issued (S118: YES), the processing of this operation example is brought to an end. On the other hand, when the instruction to finish the examination is not issued in this stage (S118: NO), current processing for the scan through the image display is continued until the stopping of the biological reaction is sensed (S115: YES).

According to this operation example, it is possible to automatically control the X-ray irradiation interval as the scan condition based on the state (occurrence/stopping) of the biological reaction of the subject E. Specifically, it is possible to acquire the image by performing the scan at relatively long irradiation intervals when the biological reaction is not occurring, and to acquire the image by performing the scan at relatively short irradiation intervals when the biological reaction is occurring. Accordingly, it is possible to reliably acquire the image in the state in which the biological reaction is occurring and to suppress the X-ray exposure when the biological reaction is not occurring. In addition, there is no need to verify an occurrence state of the biological reaction to perform an operation for switching the scan condition (X-ray irradiation interval).

(Third Operation Example)

Figure 15:
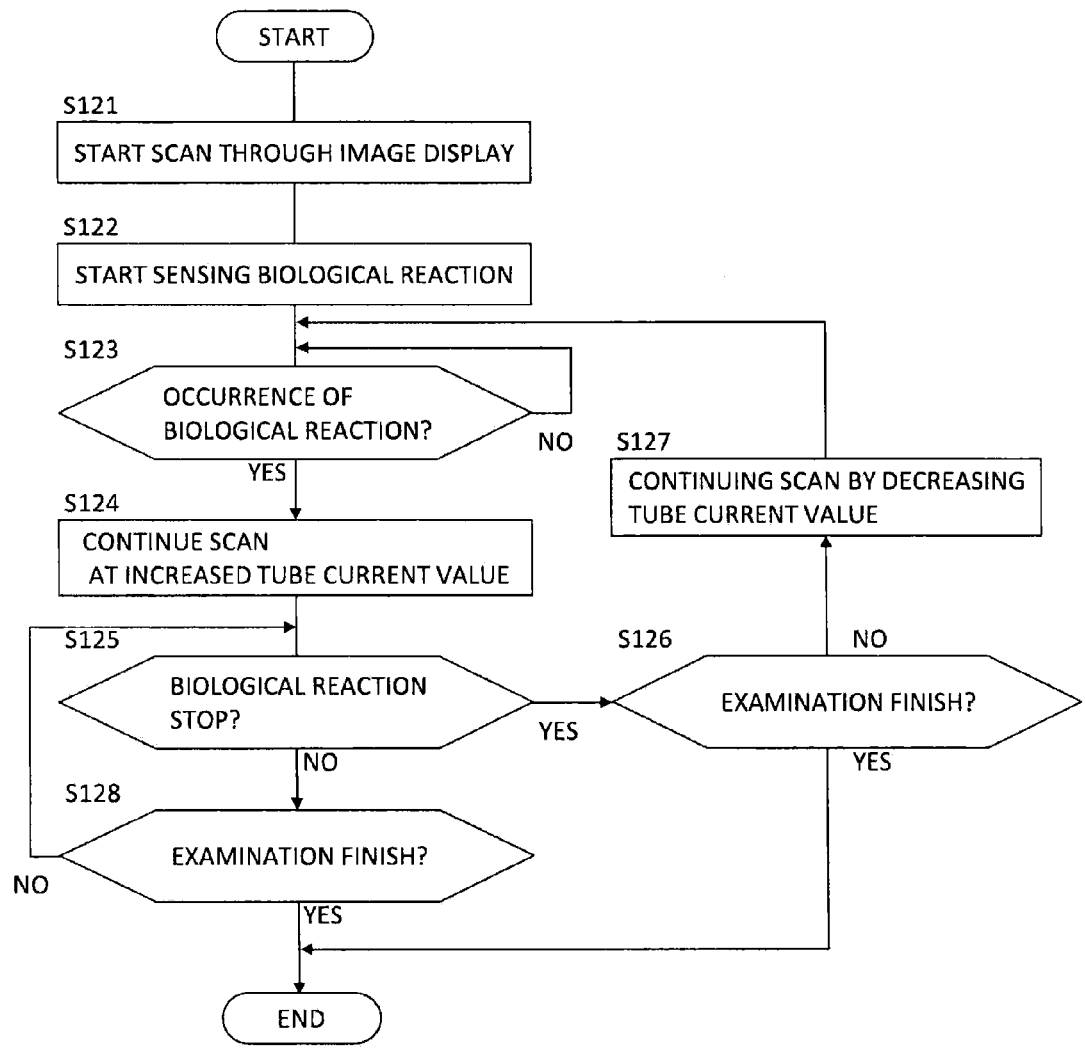
FIG. 15 is a flowchart illustrating a third operation example of the X-ray CT apparatus according to the modified example.

The third operation relates to control for changing the tube current value (scan condition) in response to the input of the biological reaction information. FIG. 15 illustrates a flow of the third operation example. Note that, the same operation as described above is only described in brief.

(S121: Start Scan through Image Display)

When a predetermined instruction to start the scan is input, the main control unit 411 starts the scan, generation of the projection data, generation of the volume data, generation of the MPR image data, and display of the MPR image. Note that, in the scan in this stage, it is assumed that a first tube current value is employed. The first tube current value, which is set relatively small, is employed in a case where the biological reaction is not occurring.

(S122: Start Sensing Biological Reaction)

The sensor unit 200 starts sensing the biological reaction of the subject E.

(S123: Sense Occurrence of Biological Reaction)

When sensing the occurrence of the biological reaction, the sensor unit 200 inputs the biological reaction information indicating the occurrence to the main control unit 411 (S123: YES).

(S124: Continue Scan at Increased Tube Current Value)

The main control unit 411 that has received the biological reaction information sends the control signal to the collection control unit 412. The collection control unit 412 generates the control signal for switching the tube current to a second tube current value, and sends the control signal to the scan control unit 42. The scan control unit 42 continues the scan by controlling the high voltage generating unit 14 to switch the tube current from the first tube current value to the second tube current value. It is assumed that the second tube current value is larger than the first tube current value. In other words, the tube current value is increased in Step S124. Note that, the first tube current value and the second tube current value are values set in advance.

(S125 to S127: Processing that Accompanies Stopping of Biological Reaction)

When sensing the stopping of the biological reaction, the sensor unit 200 inputs the biological reaction information indicating the stopping to the main control unit 411 (S125: YES). When an instruction to finish the examination is issued (S126: YES), the processing of this operation example is brought to an end. On the other hand, when the instruction to finish the examination is not issued in this stage (S126: NO), the main control unit 411 sends the control signal to the collection control unit 412. The collection control unit 412 generates the control signal for switching the tube current to the first tube current value, and sends the control signal to the scan control unit 42. The scan control unit 42 continues the scan by controlling the high voltage generating unit 14 to switch the tube current from the second tube current value to the first tube current value (S127).

(S125 and S128: Processing in Case where Biological Reaction is Continuing)

When the stopping of the biological reaction is not sensed in Step S125, in other words, when the biological reaction is continuing (S125: NO), when the instruction to finish the examination is issued (S128: YES), the processing of this operation example is brought to an end. On the other hand, when the instruction to finish the examination is not issued in this stage (S128: NO), current processing for the scan through the image display is continued until the stopping of the biological reaction is sensed (S125: YES).

According to this operation example, it is possible to automatically control the tube current value as the scan condition based on the state (occurrence/stopping) of the biological reaction of the subject E. Specifically, it is possible to acquire the image by performing the scan at a relatively small tube current value when the biological reaction is not occurring, and to acquire the image by performing the scan at a relatively large tube current value when the biological reaction is occurring. Accordingly, it is possible to acquire a high-quality image when the biological reaction is occurring and to suppress the X-ray exposure when the biological reaction is not occurring. In addition, there is no need to verify an occurrence state of the biological reaction to perform an operation for switching the scan condition (tube current).

(Fourth Operation Example)

Figure 16:
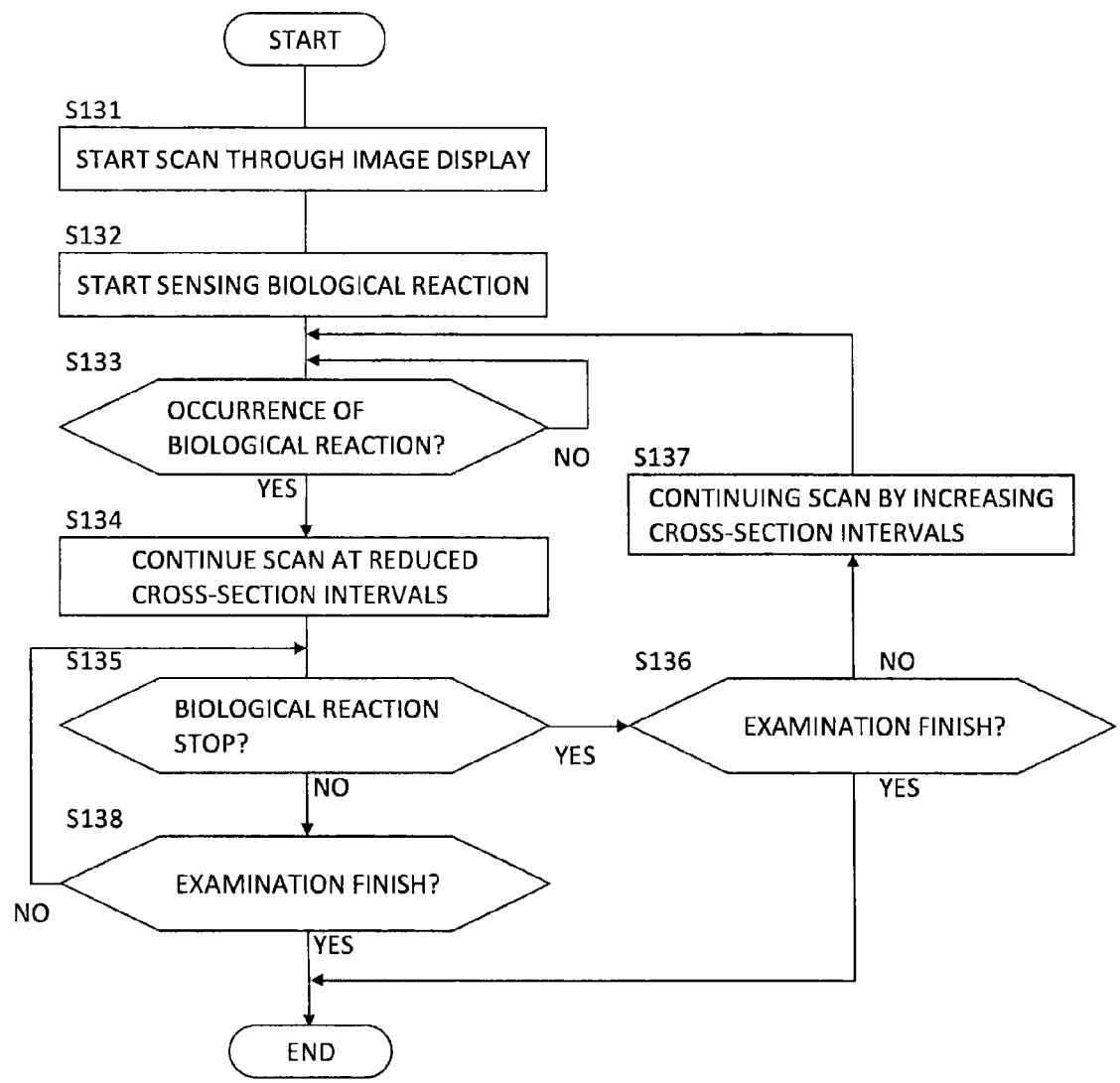
FIG. 16 is a flowchart illustrating a fourth operation example of the X-ray CT apparatus according to the modified example.

The fourth operation relates to control for changing the cross-section interval (reconstruction condition) in response to the input of the biological reaction information. FIG. 16 illustrates a flow of the fourth operation example. Note that, the same operation as described above is only described in brief.

(S131: Start Scan through Image Display)

When a predetermined instruction to start the scan is input, the main control unit 411 starts the scan, generation of the projection data, generation of the volume data (reconstruction processing), generation of the MPR image data, and display of the MPR image. Note that, in the reconstruction processing in this stage, it is assumed that a first cross-section interval is employed. The first cross-section interval, which is set relatively wide, is employed in a case where the biological reaction is not occurring.

(S132: Start Sensing Biological Reaction)

The sensor unit 200 starts sensing the biological reaction of the subject E.

(S133: Sense Occurrence of Biological Reaction)

When sensing the occurrence of the biological reaction, the sensor unit 200 inputs the biological reaction information indicating the occurrence to the main control unit 411 (S133: YES).

(S134: Continue Reconstruction Processing at Reduced Cross-Section Intervals)

The main control unit 411 that has received the biological reaction information sends the control signal to the processing control unit 414. The processing control unit 414 generates the control signal for switching the cross-section interval to a second cross-section interval, and sends the control signal to the reconstruction processing unit 432. The reconstruction processing unit 432 continues the reconstruction processing by switching the cross-section interval from the first cross-section interval to the second cross-section interval. It is assumed that the second cross-section interval is narrower than the first cross-section interval. In other words, the cross-section interval is reduced in Step S134. Note that, the first cross-section interval and the second cross-section interval are values set in advance.

(S135 to S137: Processing that Accompanies Stopping of Biological Reaction)

When sensing the stopping of the biological reaction, the sensor unit 200 inputs the biological reaction information indicating the stopping to the main control unit 411 (S135: YES). When an instruction to finish the examination is issued (S136: YES), the processing of this operation example is brought to an end. On the other hand, when the instruction to finish the examination is not issued in this stage (S136: NO), the main control unit 411 sends the control signal to the processing control unit 414. The processing control unit 414 generates the control signal for switching the cross-section interval to the first cross-section interval, and sends the control signal to the reconstruction processing unit 432. The reconstruction processing unit 432 continues the reconstruction processing by switching the cross-section interval from the second cross-section interval to the first cross-section interval (S137).

(S135 and S138: Processing in Case where Biological Reaction is Continuing)

When the stopping of the biological reaction is not sensed in Step S135, in other words, when the biological reaction is continuing (S135: NO), when the instruction to finish the examination is issued (S138: YES), the processing of this operation example is brought to an end. On the other hand, when the instruction to finish the examination is not issued in this stage (S138: NO), current processing for the scan through the image display is continued until the stopping of the biological reaction is sensed (S135: YES).

According to this operation example, it is possible to automatically control the cross-section interval as the reconstruction condition based on the state (occurrence/stopping) of the biological reaction of the subject E. Specifically, it is possible to form the image by performing the reconstruction processing at relatively wide cross-section intervals when the biological reaction is not occurring, and to form the image by performing the reconstruction processing at relatively narrow cross-section intervals when the biological reaction is occurring. Accordingly, it is possible to reliably acquire a plurality of images enabling a detailed observation of the subject E when the biological reaction is occurring and to suppress the X-ray exposure when the biological reaction is not occurring. In addition, there is no need to verify an occurrence state of the biological reaction to perform an operation for switching the reconstruction condition (cross-section interval).

(Fifth Operation Example)

Figure 17:
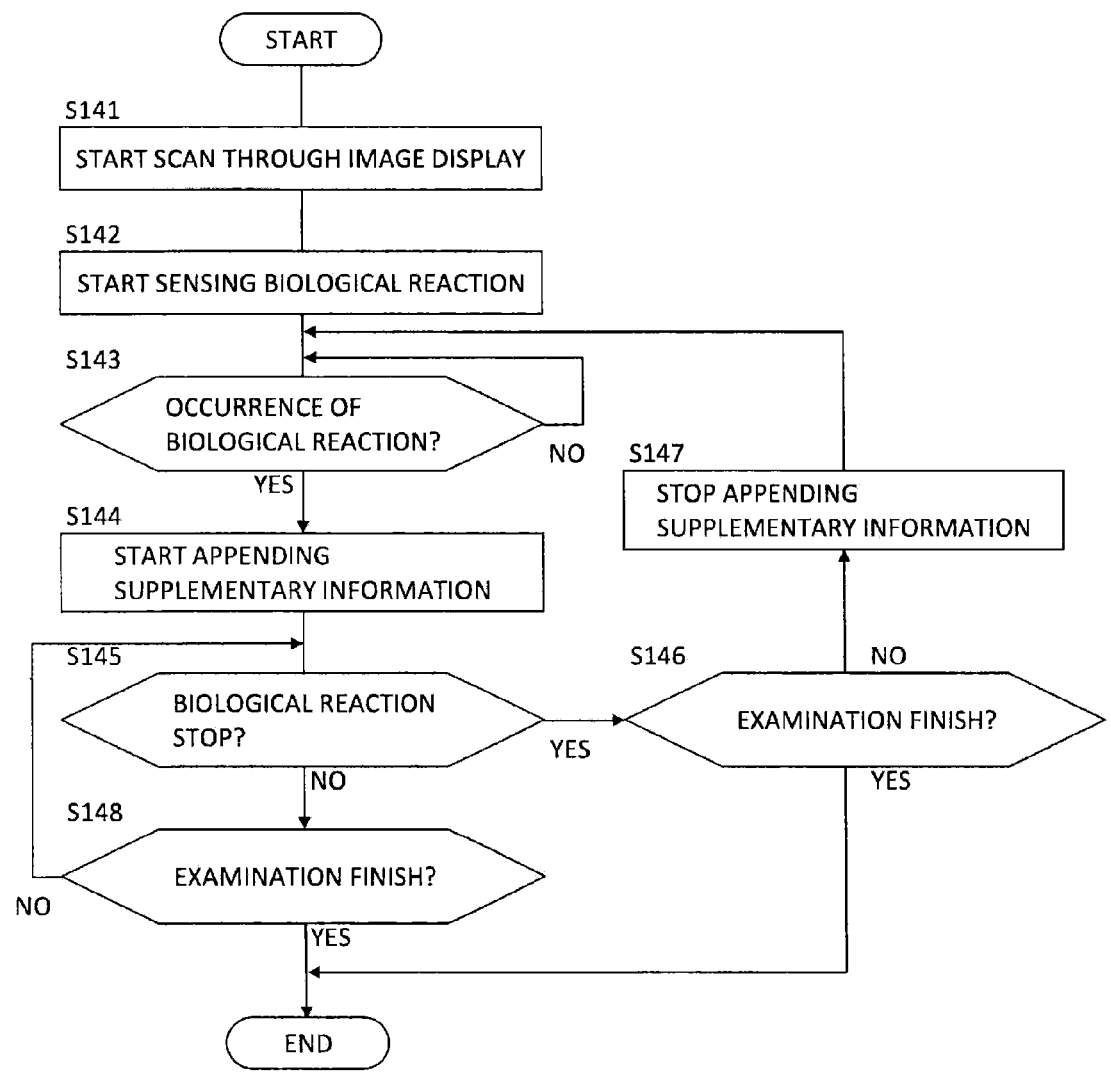
FIG. 17 is a flowchart illustrating a fifth operation example of the X-ray CT apparatus according to the modified example.

The fifth operation relates to control for appending the supplementary information to the image data in response to the input of the biological reaction information. FIG. 17 illustrates a flow of the fifth operation example. Note that, the same operation as described above is only described in brief.

(S141: Start Scan through Image Display)

When a predetermined instruction to start the scan is input, the main control unit 411 starts the scan, the generation of the projection data, the generation of the volume data, the generation of the MPR image data, and the display of the MPR image. In this stage, it is assumed that processing for appending the supplementary information to the volume data is not executed.

(S142: Start Sensing Biological Reaction)

The sensor unit 200 starts sensing the biological reaction of the subject E.

(S143: Sense Occurrence of Biological Reaction)

When sensing the occurrence of the biological reaction, the sensor unit 200 inputs the biological reaction information indicating the occurrence to the main control unit 411 (S143: YES).

(S144: Start Appending Supplementary Information)

The main control unit 411 that has received the biological reaction information sends the control signal to the processing control unit 414. The processing control unit 414 generates the control signal for appending the supplementary information to the volume data, and sends the control signal to the information adding unit 439. The information adding unit 439 appends the predetermined supplementary information to the volume data generated by the reconstruction processing unit 432. In this operation example, the volume data is repeatedly generated. The information adding unit 439 appends the supplementary information to each piece of volume data based on the detection data collected while the biological reaction is occurring. Further, in this operation example, the supplementary information is appended to the volume data, but the supplementary information may be appended to the MPR image data.

(S145 to S147: Processing that Accompanies Stopping of Biological Reaction)

When sensing the stopping of the biological reaction, the sensor unit 200 inputs the biological reaction information indicating the stopping to the main control unit 411 (S145: YES). When the instruction to finish the examination is issued (S146: YES), the processing of this operation example is brought to an end. On the other hand, when the instruction to finish the examination is not issued in this stage (S146: NO), the main control unit 411 sends the control signal to the processing control unit 414. The processing control unit 414 generates the control signal for stopping the processing for appending the supplementary information to the volume data, and sends the control signal to the information adding unit 439. The information adding unit 439 stops the processing for appending the supplementary information to the volume data (S147).

(S145 and S148: Processing in Case where Biological Reaction is Continuing)

When the stopping of the biological reaction is not sensed in Step S145, in other words, when the biological reaction is continuing (S145: NO), when the instruction to finish the examination is issued (S148: YES), the processing of this operation example is brought to an end. On the other hand, when the instruction to finish the examination is not issued in this stage (S148: NO), current processing for the scan through the image display and for appending the supplementary information is continued until the stopping of the biological reaction is sensed (S145: YES).

According to this operation example, it is possible to append the supplementary information to the image data based on the detection data collected while the biological reaction of the subject E is occurring. Accordingly, it is possible to easily determine whether arbitrary image data indicates the state of the subject E in the case where the biological reaction is occurring or indicates the state of the subject E in the case where the biological reaction is not occurring. Further, there is no need to verify the occurrence state of the biological reaction to perform an operation for appending the supplementary information. In addition, the main control unit 411 can store the image data and the supplementary information in the storage unit 44 or an external storage device in association with each other, and can switch the display mode depending on presence/absence of the supplementary information when the image is viewed later. Therefore, even when the image is viewed later, it is possible to easily determine whether or not the image is obtained during the occurrence of the biological reaction. This holds true of a case where the image is viewed by another device. Note that, presence/absence of the occurrence of the biological reaction can be grasped by displaying display information based on the supplementary information.

(Sixth Operation Example)

Figure 18:
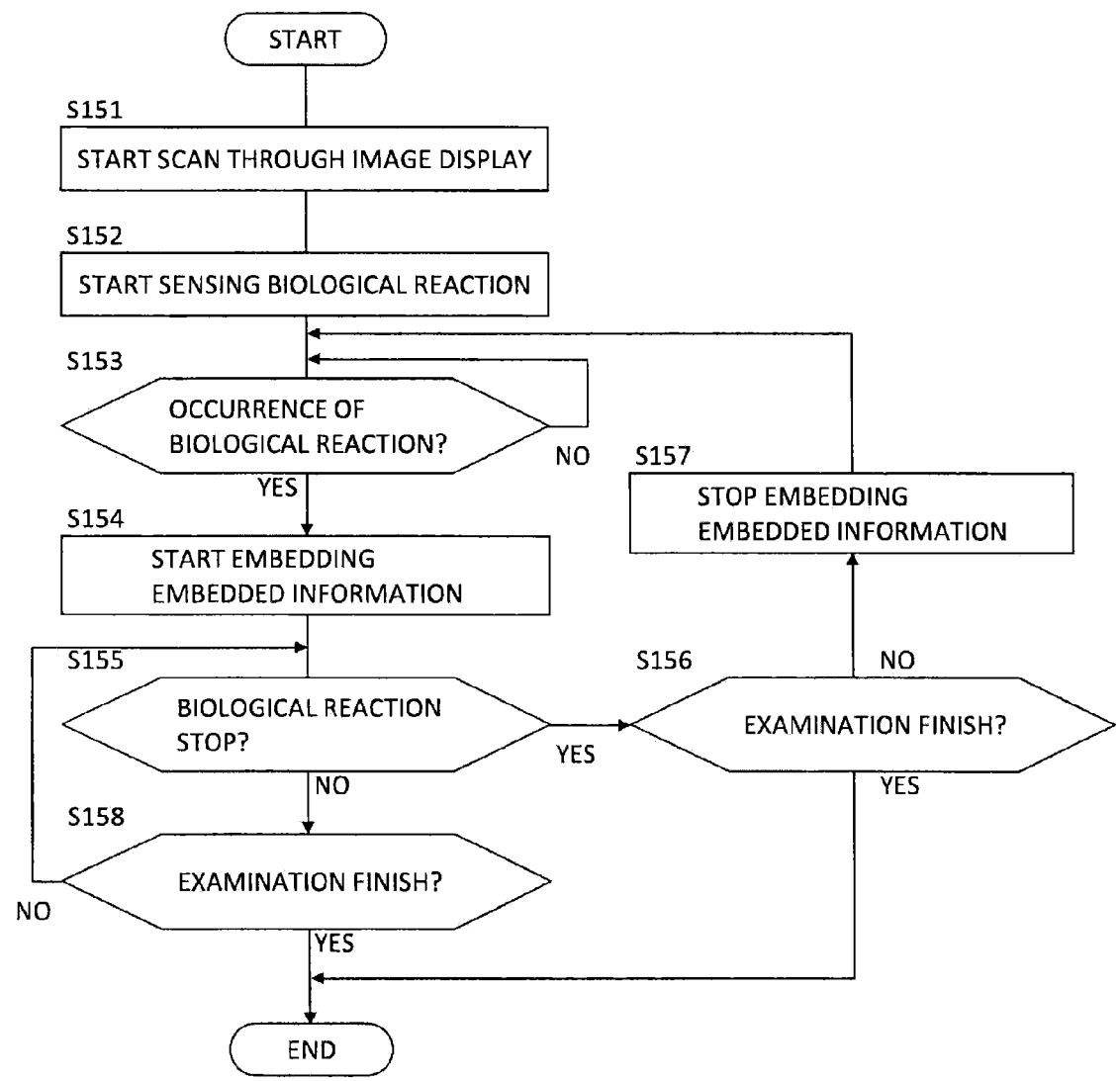
FIG. 18 is a flowchart illustrating a sixth operation example of the X-ray CT apparatus according to the modified example.

The sixth operation relates to control for embedding the embedded information in the image data in response to the input of the biological reaction information. FIG. 18 illustrates a flow of the sixth operation example. Note that, the same operation as described above is only described in brief.

(S151: Start Scan through Image Display)

When a predetermined instruction to start the scan is input, the main control unit 411 starts the scan, the generation of the projection data, the generation of the volume data, the generation of the MPR image data, and the display of the MPR image. In this stage, it is assumed that processing for embedding the embedded information in the volume data is not executed.

(S152: Start Sensing Biological Reaction)

The sensor unit 200 starts sensing the biological reaction of the subject E.

(S153: Sense Occurrence of Biological Reaction)

When sensing the occurrence of the biological reaction, the sensor unit 200 inputs the biological reaction information indicating the occurrence to the main control unit 411 (S153: YES).

(S154: Start Embedding Embedded Information)

The main control unit 411 that has received the biological reaction information sends the control signal to the processing control unit 414. The processing control unit 414 generates the control signal for embedding the embedded information in the volume data, and sends the control signal to the information adding unit 439. The information adding unit 439 embeds the predetermined embedded information in the volume data generated by the reconstruction processing unit 432. In this operation example, the volume data is repeatedly generated. The information adding unit 439 embeds the embedded information in each piece of volume data based on the detection data collected while the biological reaction is occurring. Further, in this operation example, the embedded information is embedded in the volume data, but the embedded information may be embedded in the MPR image data.

(S155 to S157: Processing that Accompanies Stopping of Biological Reaction)

When sensing the stopping of the biological reaction, the sensor unit 200 inputs the biological reaction information indicating the stopping to the main control unit 411 (S155: YES). When the instruction to finish the examination is issued (S156: YES), the processing of this operation example is brought to an end. On the other hand, when the instruction to finish the examination is not issued in this stage (S156: NO), the main control unit 411 sends the control signal to the processing control unit 414. The processing control unit 414 generates the control signal for stopping the processing for embedding the embedded information in the volume data, and sends the control signal to the information adding unit 439. The information adding unit 439 stops the processing for embedding the embedded information in the volume data (S157).

(S155 and S158: Processing in Case where Biological Reaction is Continuing)

When the stopping of the biological reaction is not sensed in Step S155, in other words, when the biological reaction is continuing (S155: NO), when the instruction to finish the examination is issued (S158: YES), the processing of this operation example is brought to an end. On the other hand, when the instruction to finish the examination is not issued in this stage (S158: NO), current processing for the scan through the image display and for embedding the embedded information is continued until the stopping of the biological reaction is sensed (S155: YES).

According to this operation example, it is possible to embed the embedded information in the image data based on the detection data collected while the biological reaction of the subject E is occurring. Accordingly, it is possible to easily determine whether the arbitrary image data indicates the state of the subject E in the case where the biological reaction is occurring or indicates the state in the case where the biological reaction is not occurring. Further, there is no need to verify the occurrence state of the biological reaction to perform an operation for embedding the embedded information. In addition, the main control unit 411 can store the image data, in which the embedded information is embedded, in the storage unit 44 or the external storage device. Therefore, even when the image is viewed later, it is possible to easily determine whether or not the image is obtained during the occurrence of the biological reaction. This holds true of the case where the image is viewed by another device. Note that, the presence/absence of the occurrence of the biological reaction can be grasped by displaying the display information based on the embedded information.

(Seventh Operation Example)

Figure 19:
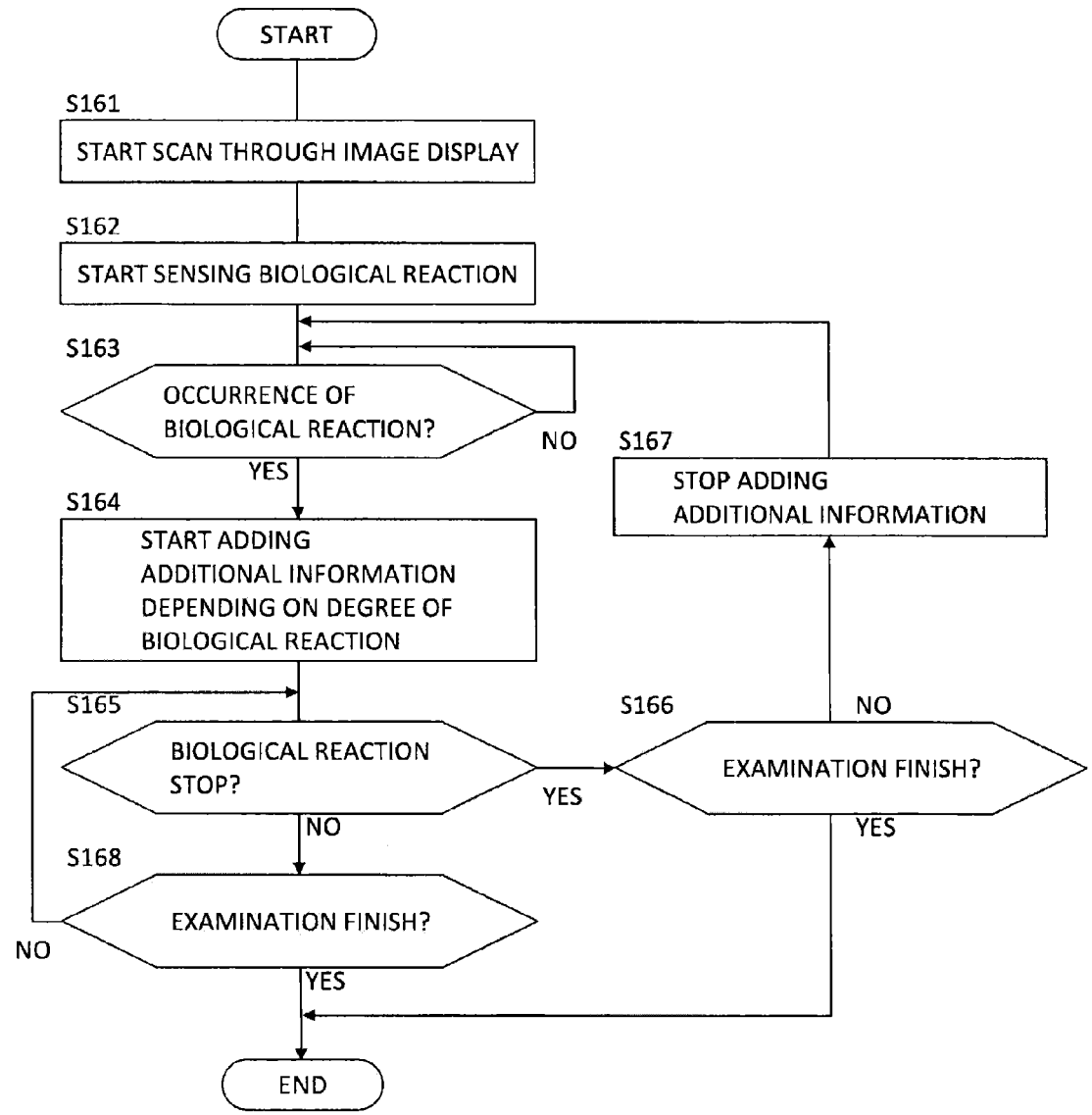
FIG. 19 is a flowchart illustrating a seventh operation example of the X-ray CT apparatus according to the modified example.

The seventh operation example relates to control for adding to the image data the additional information that differs depending on the degree information on the biological reaction. FIG. 19 illustrates a flow of the seventh operation example. Note that, the same operation as described above is only described in brief.

(S161: Start Scan through Image Display)

When a predetermined instruction to start the scan is input, the main control unit 411 starts the scan, the generation of the projection data, the generation of the volume data, the generation of the MPR image data, and the display of the MPR image. In this stage, it is assumed that processing for adding the additional information to the volume data is not executed.

(S162: Start Sensing Biological Reaction)

The sensor unit 200 starts sensing the biological reaction of the subject E.

(S163: Sense Occurrence of Biological Reaction)

When sensing the occurrence of the biological reaction, the sensor unit 200 inputs to the main control unit 411 the biological reaction information including the degree information indicating the degree of the biological reaction (S163: YES).

(S164: Start Adding Additional Information Depending on Degree of Biological Reaction)

The main control unit 411 that has received the biological reaction information generates the control signal based on the degree information included in the biological reaction information, and sends the control signal to the processing control unit 414. The processing control unit 414 generates the control signal for adding the additional information based on the control signal, in other words, the additional information based on the degree of the biological reaction, to the volume data, and sends the control signal to the information adding unit 439. In this case, the processing control unit 414 stores in advance table information in which, for example, the degree of the biological reaction is associated with a mode of the additional information, and refers to the table information to identify the additional information corresponding to a degree indicated in the degree information. Then, the processing control unit 414 generates the control signal based on the identified additional information, and sends the control signal to the information adding unit 439. The information adding unit 439 adds the additional information to the volume data generated by the reconstruction processing unit 432. In this operation example, the volume data is repeatedly generated. The information adding unit 439 adds, to each piece of volume data based on the detection data collected while the biological reaction is occurring, the additional information corresponding to the degree information at the time of the collection. Further, in this operation example, the additional information is added to the volume data, but the additional information may be added to the MPR image data.

(S165 to S167: Processing that Accompanies Stopping of Biological Reaction)

When sensing the stopping of the biological reaction, the sensor unit 200 inputs the biological reaction information indicating the stopping to the main control unit 411 (S165: YES). When the instruction to finish the examination is issued (S166: YES), the processing of this operation example is brought to an end. On the other hand, when the instruction to finish the examination is not issued in this stage (S166: NO), the main control unit 411 sends the control signal to the processing control unit 414. The processing control unit 414 generates the control signal for stopping the processing for adding the additional information to the volume data, and sends the control signal to the information adding unit 439. The information adding unit 439 stops the processing for adding the additional information to the volume data (S167).

(S165 and S168: Processing in Case where Biological Reaction is Continuing)

When the stopping of the biological reaction is not sensed in Step S165, in other words, when the biological reaction is continuing (S165: NO), when the instruction to finish the examination is issued (S168: YES), the processing of this operation example is brought to an end. On the other hand, when the instruction to finish the examination is not issued in this stage (S168: NO), current processing for the scan through the image display and for adding the additional information based on the degree information is continued until the stopping of the biological reaction is sensed (S165: YES).

According to this operation example, it is possible to add the additional information to the image data based on the detection data collected while the biological reaction of the subject E is occurring. Accordingly, it is possible to easily determine whether arbitrary image data indicates the state of the subject E in the case where the biological reaction is occurring or indicates the state of the subject E in the case where the biological reaction is not occurring. In addition, in this operation example, the additional information that differs depending on the degree of the biological reaction can be added, and hence it is possible to grasp the degree of the biological reaction at a time of the scan for acquiring the image data. Further, there is no need to verify the occurrence state of the biological reaction (presence/absence of the occurrence and the degree thereof) to perform an operation for adding the additional information. In addition, the main control unit 411 can store the image data, to which the additional information is added, in the storage unit 44 or the external storage device. Therefore, even when the image is viewed later, it is possible to easily determine whether or not the image is obtained during the occurrence of the biological reaction, and further to easily grasp the degree of the biological reaction at the time of acquiring the image. This holds true of the case where the image is viewed by another device. Note that, the presence/absence of the occurrence of the biological reaction can be grasped by displaying the display information based on the additional information. Further, the degree of the biological reaction can be grasped by displaying the display information (for causing the display mode to differ depending on the degree) based on the additional information added based on the degree information.

(Action/Effects)

Action and effects of the X-ray CT apparatus according to the modified example are described.

The X-ray CT apparatus includes the collection unit, the processing unit, the input unit, the display unit, the display control unit, and the control unit. The collection unit includes the pedestal apparatus 10 (and the bed apparatus 30), and collects the data by irradiating the subject E with the X-rays. More specifically, the collection unit collects the data by scanning the subject E with the X-rays. The processing unit includes the processing unit 43 (in particular, the reconstruction processing unit 432 and the information adding unit 439), and forms the image of the subject E by processing the data collected by the collection unit. The input unit includes the sensor unit 200 or the operation unit 46, and inputs the biological reaction information indicating the state of a predetermined biological reaction of the subject E. The display control unit includes the display control unit 413, and displays the information on the display unit 45. The control unit includes the control unit 41, and controls at least one of the collection unit, the processing unit, and the display control unit based on the biological reaction information input by the input unit. According to the X-ray CT apparatus, the respective components of the apparatus can be controlled based on the biological reaction information, and hence it is possible to perform the control based on the state of the biological reaction of the subject E.

The control unit can start or stop the scan by controlling the collection unit based on the input biological reaction information. Further, the control unit can be configured to start or stop the scan in response to the input of the biological reaction information indicating the occurrence of the biological reaction. In addition, the input unit can be configured to input the respiration state information indicating the respiration state as the biological reaction information, and the control unit can be configured to start the scan in response to the input of the respiration state information indicating the disturbance of the respiration and to stop the scan in response to the input of the respiration state information indicating the recovery of the respiration. According to the X-ray CT apparatus, it is possible to control the starting/stopping of the scan based on the state of the biological reaction of the subject E.

The control unit can continue the scan by changing the scan condition based on the biological reaction information input when the scan is being performed. In addition, the scan condition includes the time interval (irradiation interval) at which the X-rays are irradiated, and the control unit can be configured to reduce the irradiation interval in response to the fact that the biological reaction information indicating the occurrence of the biological reaction is input when the scan is being performed. Further, the scan condition includes the tube current value, and the control unit can be configured to increase the tube current value in response to the fact that the biological reaction information indicating the occurrence of the biological reaction is input when the scan is being performed. According to the X-ray CT apparatus, the scan can be performed by controlling the scan condition based on the state of the biological reaction of the subject E.

In a case where the biological reaction information is input when the scan is being performed, the control unit can control the reconstruction processing unit 432 so that the reconstruction condition used in the reconstruction processing for the projection data based on the data collected before the input of the biological reaction information differs from the reconstruction condition used in the reconstruction processing for the projection data based on the data collected after the input. At this time, the reconstruction condition includes the cross-section interval, and the control unit can be configured to reduce the cross-section interval in response to the fact that the biological reaction information indicating the occurrence of the biological reaction is input when the scan is being performed. According to the X-ray CT apparatus, the reconstruction processing can be performed by controlling the reconstruction condition based on the state of the biological reaction of the subject E.

In the case where the biological reaction information is input when the scan is being performed, the control unit can cause the information adding unit 439 (data processing unit) to execute the processing for adding the predetermined additional information based on the biological reaction information to the image data. Further, the control unit can be configured to cause the information adding unit 439 to execute processing for appending the predetermined supplementary information serving as the additional information to the image data. Further, the control unit can be configured to cause the information adding unit 439 to execute processing for embedding predetermined embedded information serving as the additional information in the image data. In addition, in the case where the reconstruction processing unit 432 generates the volume data as the image data, the control unit can be configured to cause the information adding unit 439 to execute the processing for embedding the embedded information in the position within the volume data included in the arbitrary cross-section of the volume data. According to the X-ray CT apparatus, the additional information corresponding to the biological reaction of the subject E can be added to the image data, and hence it is possible to grasp which state the biological reaction is in when the image data is acquired. Further, by configuring the display unit 45 to display the image based on the image data and the display information based on the additional information, it is possible to grasp, at a glance, which state the biological reaction is in when the image data is acquired.

In the case where the biological reaction information includes the degree information, the control unit can control the data processing unit to add the additional information that differs depending on the degree of the biological reaction indicated by the degree information. In addition, the control unit can be configured to control the display control unit to display the image based on the image data and the display information in the mode corresponding to the degree information, on the display unit. According to the X-ray CT apparatus, it is possible to grasp which degree of the biological reaction is occurring when the image data is acquired.

The input unit may include the sensor unit 200 (sensing unit) for monitoring the state of the subject E, sensing the biological reaction, and inputting the signal serving as the biological reaction information. According to the X-ray CT apparatus, it is possible to automatically sense the biological reaction and to control the respective components of the apparatus based on the detection result therefor. The X-ray CT apparatus described above is particularly effective for the examination performed by referring to the biological reaction to be judged objectively.

The input unit may include the operation unit 46 (operation unit) for inputting the signal serving as the biological reaction information in response to an operation performed by an operator. The X-ray CT apparatus described above is particularly effective for the examination performed by referring to the biological reaction to be judged subjectively.

The input unit can be configured to input pain state information indicating the biological reaction that accompanies an occurrence state of the pain, as the biological reaction information. According to the X-ray CT apparatus, it is possible to associate the state of the pain with the image data.

The X-ray CT apparatus have been described above as the embodiments, but the same configuration can be applied to the X-ray machine. In the X-ray machine as another embodiment, the collection unit includes an X-ray generating unit including an X-ray tube and an X-ray detector (planar detector) for detecting the X-rays that have passed through the subject. The processing unit, the input unit, the display unit, the display control unit, and the control unit are substantially the same as those of the X-ray CT apparatus according to the embodiments. However, a specific configuration of the processing unit is different. In other words, it is assumed that the processing unit of the X-ray machine forms the image of the subject by processing the data collected by the X-ray detector. According to such an X-ray machine as the another embodiment, it is possible to obtain the same action/effects as the above-mentioned X-ray CT apparatus. Further, an arbitrary configuration and control described in the above-mentioned X-ray CT apparatus according to the embodiments can be implemented by being applied to the X-ray machine.

The medical image diagnostic apparatus according to the embodiments or the modified example (first medical image diagnostic apparatus) can transmit the timing information and at least one of the internal image and the outer appearance image to another medical image diagnostic apparatus (second medical image diagnostic apparatus).

The second medical image diagnostic apparatus may employ a modality of an arbitrary type such as the X-ray CT apparatus, the X-ray machine, a magnetic resonance imaging (MRI) apparatus, a positron emission tomography (PET) apparatus, a single photon emission computed tomography (SPECT) apparatus, and an ultrasonography apparatus.

The second medical image diagnostic apparatus acquires the occurrence timing of the biological reaction based on the information received from the first medical image diagnostic apparatus, and performs the photographing based on the occurrence timing. Accordingly, also on another medical image diagnostic apparatus, the photographing can be performed at the timing corresponding to the occurrence of the biological reaction. Further, it is possible to grasp the relationship between the action state of the body and the occurrence timing of the biological reaction.

By superimposing at least one of the internal image and the outer appearance image obtained by the first medical image diagnostic apparatus on the image acquired by the second medical image diagnostic apparatus, the second medical image diagnostic apparatus can display a fusion image thereof. A publicly-known method can be used as fusion image displaying processing including processing for positioning the images.

The timing information and at least one of the internal image and the outer appearance image acquired by the medical image diagnostic apparatus according to the embodiments or the modified example can be used for medical practice other than medical image diagnosis. Application examples thereof include design of an artificial joint, rehabilitation, and informed consent.

In the design of the artificial joint, reference can be made to the timing at which the pain occurs and to a moveable range of the joint that can be grasped based on the plurality of internal images. The rehabilitation can be carried out while grasping how much the joint is bent when the pain occurs (to which extent). In the informed consent, a comprehensible explanation can be given of the relationship between the action state of the body and the occurrence timing of the biological reaction.

In each of the above-mentioned embodiments and modified example, the example of the X-ray CT apparatus has been described in detail, but the same configuration can be applied to the X-ray machine. The X-ray machine outputs X-rays from the X-ray tube, and detects and visualizes the X-rays that have passed through the subject by using the X-ray detector (imaging plate), to thereby acquire the internal image. The X-ray machine not only forms an image along a plane orthogonal to a direction that connects between the X-ray tube and the X-ray detector but also restructures a three-dimensional image from a plurality of images photographed from different directions. The X-ray machine is used as the "internal image acquiring unit".

It is possible to use the medical image diagnostic apparatus according to the embodiments and the modified example in the following manner. First, while instructing an examinee to bend and stretch the joint, without administering anesthesia thereto, first photographing is performed to acquire the image in the time phase corresponding to the occurrence timing of the pain. This image may be the internal image or the outer appearance image. Second photographing is performed by administering anesthesia to the examinee, which (almost) keeps the examinee from feeling the pain. In the second photographing, it is possible to grasp the bent state of the joint by comparing the image obtained by the first photographing with a newly-acquired image. Therefore, it is possible to perform the photographing while maintaining the bent state causing the pain and to perform the photographing while instructing the examinee to gradually bend and stretch the joint. Accordingly, the state of the joint causing the pain can be examined in detail.

Further, in a case where the same body part of the subject is examined a plurality of times as in preoperative/postoperative observations and follow-ups, the image at the occurrence timing of the biological reaction obtained in the past can be acquired by using the image in the time phase corresponding to the occurrence timing for the current examination. Accordingly, a change in the state of an affected area can be grasped in detail. In addition, a relationship between the change in the state of the affected area and the biological reaction can also be grasped in detail.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising:
   a collection unit configured to collect data by performing irradiation of X-rays to a body part of a subject with moving a joint of the body part;
   an input unit configured to input pain state information indicating a biological reaction that accompanies movement of the joint, is different from a reaction in a steady state, and is sensed based on a threshold value; and
   a control unit configured to control the collection unit based on the input pain state information from the start of the irradiation to the end of the irradiation.

2. A medical image diagnostic apparatus according to claim 1, wherein the control unit controls one of starting and stopping of the irradiation of the X-rays to be performed by the collection unit based on the input pain state information.

3. A medical image diagnostic apparatus according to claim 2, wherein the control unit controls the one of starting and stopping of the irradiation of the X-rays in response to the input of the pain state information.

4. A medical image diagnostic apparatus according to claim 3, wherein:
   the input unit is configured to input respiration state information indicating a respiration state as the pain state information; and
   the control unit starts the irradiation of the X-rays in response to the input of the respiration state information indicating a change in respiration.

5. A medical image diagnostic apparatus according to claim 1, wherein the control unit continues the irradiation of the X-rays with changing an X-ray irradiation condition based on the pain state information input when the irradiation of the X-rays is being performed.

6. A medical image diagnostic apparatus according to claim 5, wherein:
   the X-ray irradiation condition comprises a time interval for applying the X-rays; and
   the control unit reduces the time interval in response to the input of the pain state information indicating an occurrence of the biological reaction performed when the irradiation of the X-rays is being performed.

7. A medical image diagnostic apparatus according to claim 5, wherein:
   the collection unit comprises: an X-ray generating unit; and a high voltage generating unit configured to supply power for generating the X-rays to the X-ray generating unit;
   the X-ray irradiation condition comprises a tube current value indicating a current value of an electron current within the X-ray generating unit; and
   the control unit increases the tube current value in response to the input of the pain state information indicating an occurrence of the biological reaction performed when the irradiation of the X-rays is being performed.

8. A medical image diagnostic apparatus according to claim 1, further comprising:
   a processing unit configured to process the collected data to form a plurality of internal images indicating the body part and comprising: a pre-processing unit configured to generate projection data by subjecting the collected data to pre-processing; and
   a reconstruction processing unit configured to generate image data by subjecting the generated projection data to reconstruction processing based on a reconstruction condition, wherein
   in a case where the pain state information is input when the irradiation of the X-rays is being performed, the control unit controls the reconstruction processing unit to separate the reconstruction condition used in the reconstruction processing for the projection data based on the data collected before the input of the pain state information from the reconstruction condition used in the reconstruction processing for the projection data based on the data collected after the input.

9. A medical image diagnostic apparatus according to claim 8, wherein:
   the reconstruction condition comprises a cross-section interval between tomographic images to be restructured; and
   the control unit reduces the cross-section interval in response to the input of the pain state information indicating an occurrence of the biological reaction performed when the irradiation of the X-rays is being performed.

10. A medical image diagnostic apparatus according to claim 8, wherein the processing unit comprises a processing unit of an X-ray CT apparatus for restructuring the data collected by the collection unit to form the plurality of internal images.

11. A medical image diagnostic apparatus according to claim 8, wherein:
    the collection unit performs one of continuous irradiation of X-rays and intermittent irradiation of X-rays to the subject, and detects the X-rays that have passed through the subject; and
    the processing unit comprises a processing unit of an X-ray machine for forming the plurality of internal images along a plane substantially orthogonal to an irradiation direction of the X-rays.

12. A medical image diagnostic apparatus according to claim 1, wherein further comprising:
    a processing unit configured to process the collected data to form a plurality of internal images indicating the body part and comprising:
    a pre-processing unit configured to generate projection data by subjecting the collected data to pre-processing;
    a reconstruction processing unit configured to generate image data by subjecting the generated projection data to reconstruction processing; and a data processing unit configured to process the generated image data, wherein when the pain state information is input during a period in which the X-rays are being applied, the control unit causes the data processing unit to execute processing for adding additional information based on the pain state information to the image data.

13. A medical image diagnostic apparatus according to claim 12, wherein the control unit causes the data processing unit to execute processing for appending supplementary information serving as the additional information to the image data.

14. A medical image diagnostic apparatus according to claim 12, wherein the control unit causes the data processing unit to execute processing for embedding embedded information serving as the additional information in the image data.

15. A medical image diagnostic apparatus according to claim 14, wherein:

the reconstruction processing unit generates volume data as the image data; and the control unit causes the data processing unit to execute processing for embedding the embedded information in a position within the volume data comprised in an arbitrary cross-section of the volume data.

16. A medical image diagnostic apparatus according to claim 12, wherein the control unit controls a display control unit to display, on a display unit, an image based on the image data and display information based on the additional information.

17. A medical image diagnostic apparatus according to claim 12, wherein:

the pain state information comprises degree information indicating a degree of the biological reaction; and the control unit controls the data processing unit to add the additional information that differs depending on the degree of the biological reaction indicated by the degree information.

18. A medical image diagnostic apparatus according to claim 17, further comprising a display control unit configured to display information on a display unit, wherein the control unit controls the display control unit to cause the display unit to display an image based on the image data and display information in a mode corresponding to the degree information.

19. A medical image diagnostic apparatus according to claim 1, wherein the input unit comprises a sensing unit configured to monitor a state of the subject, to sense the biological reaction, and input a signal serving as the pain state information.

20. A medical image diagnostic apparatus according to claim 1, wherein the input unit comprises an operation unit configured to input a signal serving as the pain state information in response to an operation performed by an operator.

21. A medical image diagnostic apparatus according to claim 1, further comprising:

a display control unit configured to display information on a display unit; and an outer appearance image acquiring unit configured to acquire an outer appearance image by photographing the body part of the subject at least at a photographing timing corresponding to the input of the pain state information, wherein the control unit controls the display control unit based on input biological reaction information to display the outer appearance image on the display unit.

22. A medical image diagnostic apparatus according to claim 21, further comprising a storage unit, wherein the control unit stores the outer appearance image acquired at the photographing timing and timing information indicating an occurrence timing of the biological reaction in the storage unit in association with each other, and stores at least one of a plurality of internal images in the storage unit.

23. A medical image diagnostic apparatus according to claim 22, further comprising a first identification unit for identifying one of the plurality of internal images acquired at substantially the same time as the input of the pain state information among the plurality of internal images, wherein the control unit associates the identified one of the plurality of internal images with the outer appearance image acquired at the photographing timing and the timing information.

24. A medical image diagnostic apparatus according to claim 23, wherein:

the first identification unit comprises an analysis unit configured to analyze the outer appearance image to acquire first shape information indicating a shape of the body part of the subject and to analyze the plurality of internal images to acquire second shape information indicating a shape of the body part of the subject; and the first identification unit is configured to identify one of the plurality of internal images corresponding to, among a plurality of pieces of the second shape information that have been acquired, one of the plurality of pieces of the second shape information that substantially matches the first shape information.

25. A medical image diagnostic apparatus according to claim 24, wherein the first shape information and the second shape information each comprise contour information indicating a contour shape of a body surface of the body part.

26. A medical image diagnostic apparatus according to claim 24, wherein:

the body part comprises a joint part; and the first shape information and the second shape information each comprise angle information indicating an angle formed between a bone and a bone in the joint part.

27. A medical image diagnostic apparatus according to claim 24, wherein the first feature position information and the second feature position information each comprise marker position information indicating a position of an image area representing a marker attached to a body surface of the subject.

28. A medical image diagnostic apparatus according to claim 23, wherein:

the first identification unit comprises an analysis unit configured to analyze the outer appearance image to acquire first feature position information indicating a position of a predetermined feature area within the outer appearance image, and analyze each of the plurality of internal images to acquire second feature position information indicating a position of the predetermined feature area within the each of the plurality of internal images; and the first identification unit identifies one of the plurality of internal images based on the first feature position information and the plurality of pieces of the second feature position information that have been acquired.

29. A medical image diagnostic apparatus according to claim 23, wherein the first identification unit is configured to:

enter first timing information indicating a timing at which the pain state information is input by the input unit and second timing information indicating a timing at which each of the plurality of internal images is acquired; and identify one of the plurality of internal images corresponding to the second timing information input at substantially the same time as the first timing information.

30. A medical image diagnostic apparatus according to claim 22, wherein:

the outer appearance image acquiring unit acquires the outer appearance image by photographing the body part of the subject in response to the input of the pain state information; and the control unit associates the outer appearance image with the timing information.

31. A medical image diagnostic apparatus according to claim 22, wherein:

the outer appearance image acquiring unit is repeatedly configured to photograph the body part of the subject to sequentially acquire the outer appearance images;

the medical image diagnostic apparatus further comprises a second identification unit configured to identify the outer appearance image acquired at substantially the same time as the input of the pain state information among the sequentially-acquired outer appearance images; and the control unit stores the identified outer appearance image in the storage unit as the outer appearance image acquired at the photographing timing in association with the timing information.

32. A medical image diagnostic apparatus according to claim 1, wherein the control unit causes a display unit to display a moving image based on a plurality of internal images acquired by an internal image acquiring unit and to display information indicating an occurrence timing of the biological reaction based on timing information.

* * * * *